(12) United States Patent
Subramanyam et al.

(10) Patent No.: US 8,518,944 B2
(45) Date of Patent: Aug. 27, 2013

(54) COMPOUNDS AS CASEIN KINASE INHIBITORS

(75) Inventors: Chakrapani Subramanyam, South Glastonbury, CT (US); Travis T. Wager, New London, CT (US)

(73) Assignee: Pfizer Inc., New York, NY (US)

( * ) Notice: Subject to any disclaimer, the term of this patent is extended or adjusted under 35 U.S.C. 154(b) by 284 days.

(21) Appl. No.: 12/911,030

(22) Filed: Oct. 25, 2010

(65) Prior Publication Data

US 2011/0098272 A1 Apr. 28, 2011

Related U.S. Application Data

(60) Provisional application No. 61/255,506, filed on Oct. 28, 2009.

(51) Int. Cl.
*C07D 403/14* (2006.01)
*C07D 401/14* (2006.01)
*C07D 413/14* (2006.01)
*A61K 31/506* (2006.01)

(52) U.S. Cl.
USPC ... 514/249; 514/252.02; 514/256; 514/259.3; 514/275; 544/238; 544/281; 544/295; 544/331; 544/333

(58) Field of Classification Search
USPC .............. 544/238, 281, 295, 296, 331, 333; 514/249, 252.02, 256, 259.3, 275
See application file for complete search history.

(56) References Cited

U.S. PATENT DOCUMENTS

| 6,096,739 A | 8/2000 | Feuerstein | 514/235.2 |
| 6,239,279 B1 | 5/2001 | Sisko | 546/210 |
| 2006/0223158 A1* | 10/2006 | Liu et al. | 435/194 |
| 2008/0200496 A1* | 8/2008 | Metz et al. | 514/300 |
| 2011/0183978 A1 | 7/2011 | Sudau et al. | |
| 2012/0157440 A1 | 6/2012 | Butler et al. | |

FOREIGN PATENT DOCUMENTS

WO WO9502591 1/1995

OTHER PUBLICATIONS

Damasio, Alzheimer's Disease and Related Dementias, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*
Meng et al., Entrainment of disrupted circadian behavior through inhibition of casein kinase 1 (CK1) enzymes, PNAS, vol. 107, No. 34, pp. 15240-15245, Aug. 2010.*
Antle and Silver, Trends Neurosci 28, pp. 145-151, 2005.
Lowery et al., Science, 288, pp. 483-492, 2000.
Adams et al., Biorganic & Medicinal Chemistry Letters, vol. 11, No. 21, 2001, pp. 2867-2870 (Pergamon, Elsevier Science, GB).
Walton, K.M., et al., Selective Inhibition of Casein Kinase 1 epsilon Minimally Alters Circadian Clock Period, Journal Pharmacology and Expermental Therapeutics, vol. 330, No. 2, pp. 430-439 (2009).
Bamborough, P., et al., Assessment of chemical Coverage of Kinome space and Its Implications for Kinase Drug Discovery, J. Med. Chem., vol. 51, 7898-7914 (2008).
Peifer, C., et al., 3,4-Diaryl-isoxazoles and —imidazoles as Potent Dual Inhibitors of p38a Mitogen Activated Protein Kinase and Casein Kinase 1 delta, J. Med. Chem vol. 52, 7618-7630 (2009).
Perez, D., et al., Protein Kinases CK1 and CK2 as New Targets for Neurodegenerative Diseases, Medicinal Research Reviews, vol. 31, No. 6, 924-954 (2010).
Walton, K., et al., Selective Inhibiton of Casein Kinase I epsilon Minimally Alters Circadian Clock Period, The Journal of Pharmacology and Experimental Therapeutics, vol. 330, No. 2, 430-439 (2009).

* cited by examiner

*Primary Examiner* — Deepak Rao
(74) *Attorney, Agent, or Firm* — Feng Shao

(57) ABSTRACT

Compounds and pharmaceutically acceptable salts of the compounds are disclosed, wherein the compounds have the structure of Formula I

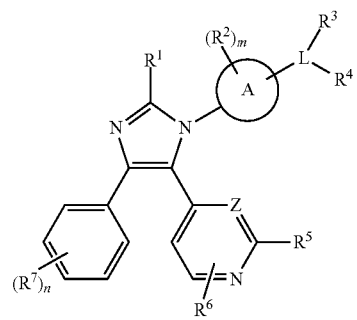

as defined in the specification. Corresponding pharmaceutical compositions, methods of treatment, methods of synthesis, and intermediates are also disclosed.

18 Claims, No Drawings

COMPOUNDS AS CASEIN KINASE INHIBITORS

CROSS REFERENCE TO PRIOR APPLICATIONS

This application claims the benefit of U.S. provisional application Ser. No. 61/255,506, filed Oct. 28, 2009, under 35 USC 119(e), which is incorporated herein by reference in its entirety.

FIELD OF THE INVENTION

This invention relates generally to pharmaceutical agents useful in the treatment and/or prevention of diseases and disorders associated with the central nervous system. More particularly, the present invention comprises compounds for the treatment of a patient suffering from a disease or disorder ameliorated by inhibition of casein kinase I delta (CK1δ) or CK1 epsilon (CK1ε) activity through the administration of a series of substituted imidazole compounds. More specifically the invention relates to 4-aryl-5-heteroaryl-1-heterocycloalkyl-imidazoles and related analogs which are inhibitors of human CK1δ or CK1ε phosphorylation.

BACKGROUND OF THE INVENTION

The circadian clock links our daily cycles of sleep and activity to the external environment. Deregulation of the clock is implicated in a number of human disorders, including depression, seasonal affective disorder, and metabolic disorders. Circadian rhythms are controlled in mammals by the master clock located in the suprachiasmatic nucleus of the hypothalamus (Antle and Silver, Trends Neurosci 28: 145-151). At the cellular level, the molecular events behind clock cycling are described by the regular increase and decrease in mRNAs and proteins that define feedback loops, resulting in approximately 24 hour cycles. The suprachiasmatic nucleus is primarily regulated, or entrained, directly by light via the retinohypothalamic tract. The cycling outputs of the suprachiasmatic nucleus, not fully identified, regulate multiple downstream rhythms, such as those in sleep and awakening, body temperature, and hormone secretion (Ko and Takahashi, Hum Mol Gen 15: R271-R277.). Furthermore, diseases such as depression, seasonal affective disorder, and metabolic disorders, may have a circadian origin (Barnard and Nolan, PLoS Genet. 2008 May; 4(5): e1000040.).

Phosphorylation of circadian clock proteins is an essential element in controlling the cyclical rhythm of the clock. CK1ε and CK1δ are closely related Ser-Thr protein kinases that serve as key clock regulators as demonstrated by mammalian mutations in each that dramatically alter the circadian period. (Lowrey et al., Science 288: 483-492). Therefore, inhibitors of CK1δ/ε have utility in treating circadian disorders. Thus it is an object of this invention to provide a series of 4-aryl-5-heteroaryl-1-heterocycloalkyl-imidazoles and related analogs that are inhibitors of CK1δ or CK1ε. This object and other objects of this invention become apparent from the detailed discussion of the invention that follows.

SUMMARY OF THE INVENTION

The invention is directed to compounds, including pharmaceutically acceptable salts thereof, having the structure of formula I:

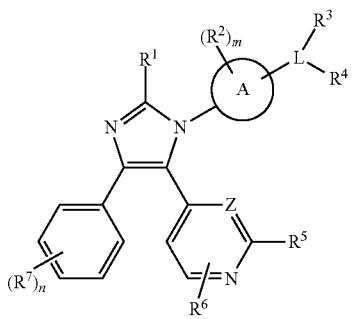

wherein A is a nitrogen-containing 4- to 7-membered heterocycloalkyl, or alternatively A can be directly fused to the ring to which it is attached through $R^1$;

L is $C_{1-3}$alkyl;

$R^1$ is hydrogen, $C_{1-3}$alkyl, or $C_{3-4}$cycloalkyl;

each $R^2$ is independently $C_{1-3}$alkyl, fluorine, hydroxyl, $C_{1-3}$alkoxy, or cyano;

$R^3$ is hydrogen, $C_{1-3}$alkyl, or $C_{3-4}$cycloalkyl;

$R^4$ is a 5- to 10-membered heteroaryl with 1 to 3 heteroatoms, optionally substituted with 1 to 3 $R^7$ substituents;

$R^5$ is hydrogen or $-N(R^8)_2$;

$R^6$ is hydrogen, halogen or $C_{1-3}$alkyl;

each $R^7$ is independently halogen, $-(CH_2)_t-F_q$, $C_{1-3}$alkyl, $-CF_3$, $-(CH_2)_tC_{3-4}$cycloalkyl, $-(CH_2)_t-O-C_{1-3}$alkyl, $-(CH_2)_t$-cyano or $-(CH_2)_t$-hydroxy;

Z is N or $CR^9$;

each $R^8$ is independently hydrogen or $C_{1-3}$alkyl;

$R^9$ is hydrogen, $C_{1-3}$alkyl, or halogen;

m is 0, 1 or 2;

n is 0, 1, or 2;

q is 1, 2, or 3;

t is 0, 1 or 2; or pharmaceutically acceptable salts thereof.

In one embodiment of the invention, A is a nitrogen-containing 4- to 7-membered heterocycloalkyl and

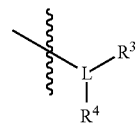

is attached to the ring N;

L is $C_1$alkyl;

each $R^2$ is independently $C_{1-3}$alkyl, or fluorine;

each $R^7$ is independently halogen, $-(CH_2)_t-F_q$, $-CF_3$, $C_{1-3}$alkyl, $-(CH_2)_t-C_{3-4}$cycloalkyl, or $-(CH_2)_t-O-C_{1-3}$ alkyl;

In another embodiment of the invention, the compounds have the structure of formula Ia:

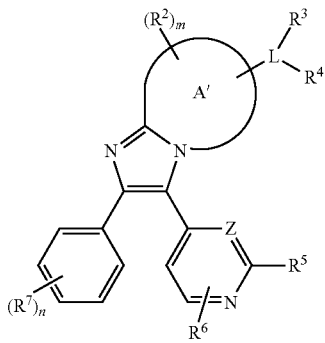

Ia wherein L is $C_{1-3}$alkyl;
$R^1$ is $C_{1-3}$alkyl, or $C_{3-4}$cycloalkyl;
each $R^2$ is independently $C_{1-3}$alkyl, fluorine, hydroxyl, $C_{1-3}$alkoxy, or cyano;
$R^3$ is hydrogen, $C_{1-3}$alkyl, or $C_{3-4}$cycloalkyl;
$R^4$ is a 5- to 10-membered heteroaryl with 1 to 3 heteroatoms, optionally substituted with 1 to 3 $R^7$ substituents;
$R^5$ is hydrogen or $N(R^8)_2$;
$R^6$ is hydrogen, halogen or $C_{1-3}$alkyl;
each $R^7$ is independently halogen, $-(CH_2)_t-F_q$, $C_{1-3}$alkyl, $-CF_3$, $-(CH_2)_t-C_{3-4}$cycloalkyl, $-(CH_2)_t-O-C_{1-3}$alkyl, $-(CH_2)_t$-cyano or $-(CH_2)_t$-hydroxy;
Z is N or $CR^9$;
each $R^8$ is independently hydrogen or $C_{1-3}$alkyl;
$R^9$ is hydrogen, $C_{1-3}$alkyl, or halogen;
m is 0, 1 or 2;
n is 0, 1, or 2;
q is 1, 2, or 3;
t is 0, 1 or 2; or pharmaceutically acceptable salts thereof.
In another embodiment of the invention A is a nitrogen-containing 4- to 6-membered heterocycloalkyl, and m=0.
In another embodiment of the invention A is a nitrogen-containing 5-membered heterocycloalkyl, wherein said heterocycloalkyl is azetidine and

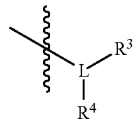

is attached to the ring N of the azetidine, and m is 0.
In another embodiment of the invention A is a nitrogen-containing 5-membered heterocycloalkyl, wherein said heterocycloalkyl is pyrrolidine and

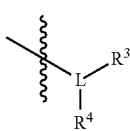

is attached to the ring N of the pyrrolidine, and m is 0.
In another embodiment of the invention A is a nitrogen-containing 6-membered heterocycloalkyl, wherein said heterocycloalkyl and

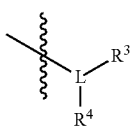

is attached to the ring N of the piperidine, and m=0.
In any of the embodiments described above, n is one and $R^7$ is halogen or $C_{1-3}$ alkyl. In any of the embodiments described above, n is one and $R^7$ is $C_{1-3}$alkyl. In any of the embodiments described, n is one and $R^7$ is halogen. In an example of this embodiment, $R^7$ is fluorine.
In any of the embodiments described above, Z is $-CR^9$; wherein $R^9$ is hydrogen and $R^5$ is hydrogen or $-N(R^8)_2$. In any of the embodiments described above, Z is $-CR^9$; wherein $R^9$ is hydrogen and $R^5$ is hydrogen. In any of the embodiments described above, Z is $-CR^9$; wherein $R^9$ is hydrogen and $R^5$ is $-N(R^8)_2$. In any of the embodiments described above, Z is $CR^9$; wherein $R^9$ is hydrogen and $R^5$ is $-N(R^8)_2$; wherein each $R^8$ is hydrogen. In any of the embodiments described above, Z is $-CR^9$; wherein $R^9$ is hydrogen and $R^5$ is $-N(R^8)_2$; wherein each $R^8$ is $C_{1-3}$alkyl. In any of the embodiments described above, Z is $-CR^9$; wherein $R^9$ is hydrogen and $R^5$ is $-N(R^8)_2$; wherein one $R^8$ is $C_{1-3}$alkyl, and the other $R^8$ is hydrogen.
In any of the embodiments described above, Z is $-CR^9$; wherein $R^9$ is $C_{1-3}$alkyl and $R^5$ is hydrogen or $-N(R^8)_2$. In any of the embodiments described above, Z is $-CR^9$; wherein $R^9$ is $C_{1-3}$alkyl and $R^5$ is hydrogen. In any of the embodiments described above, Z is $-CR^9$; wherein $R^9$ is $C_{1-3}$alkyl and $R^5$ is $-N(R^8)_2$. In any of the embodiments described above, Z is $-CR^9$; wherein $R^9$ is $C_{1-3}$alkyl and $R^5$ is $-N(R^8)_2$; wherein each $R^8$ is hydrogen. In any of the embodiments described above, Z is $-CR^9$ wherein $R^9$ is $C_{1-3}$alkyl and $R^5$ is $-N(R^8)_2$, wherein each $R^8$ is $C_{1-3}$alkyl. In any of the embodiments described above, Z is $-CR^9$ wherein $R^9$ is $C_{1-3}$alkyl and $R^5$ is $-N(R^8)_2$, wherein one $R^8$ is $C_{1-3}$alkyl, and the other $R^8$ is hydrogen.
In any of the embodiments described above, Z is $-CR^9$ wherein $R^9$ is halogen and $R^5$ is hydrogen or $-N(R^8)_2$. In any of the embodiments described above, Z is $-CR^9$ wherein $R^9$ is halogen and $R^5$ is hydrogen. In any of the embodiments described above, Z is $-CR^9$ wherein $R^9$ is halogen and $R^5$ is $-N(R^8)_2$. In any of the embodiments described above, Z is $-CR^9$ wherein $R^9$ is halogen and $R^5$ is $-N(R^8)_2$, wherein each $R^8$ is hydrogen. In another embodiment Z is $-CR^9$ wherein $R^9$ is halogen and $R^5$ is $-N(R^8)_2$, wherein each $R^8$ is $C_{1-3}$alkyl. In any of the embodiments described above, Z is $-CR^9$ wherein $R^9$ is halogen and $R^5$ is $-N(R^8)_2$, wherein one $R^8$ is $C_{1-3}$alkyl, and the other $R^8$ is hydrogen.
In any of the embodiments described above, Z is N and $R^5$ is hydrogen or $-N(R^8)_2$. In another embodiment Z is N and $R^5$ is hydrogen. In any of the embodiments described above, Z is N and $R^5$ is $-N(R^8)_2$, wherein each $R^8$ is hydrogen. In any of the embodiments described above, Z is N and $R^5$ is $-N(R^8)_2$, wherein each $R^8$ is $C_{1-3}$alkyl. In any of the embodiments described above, Z is N and $R^5$ is $-N(R^8)_2$, wherein one $R^8$ is $C_{1-3}$alkyl, and the other $R^8$ is hydrogen.
In any of the embodiments described above, $R^1$ is hydrogen or $C_{1-3}$alkyl. In any of the embodiments described above, $R^1$ is hydrogen. In any of the embodiments described above, $R^1$ is $C_{1-3}$alkyl.
In any of the embodiments described above, $R^4$ is a 5- to 10-membered heteroaryl with 1 heteroatom and is optionally substituted with 1 to 3 $R^7$ substituents; wherein each $R^7$ is independently halogen, $C_{1-3}$alkyl, $-(CH_2)_t-F_q$, $-CF_3$, $-(CH_2)_t-C_{3-4}$cycloalkyl, or $-(CH_2)_t-O-C_{1-3}$alkyl. In any of the embodiments described above, $R^4$ is a 5- to 10-membered heteroaryl with 2 heteroatoms and is optionally substituted with 1 to 3 $R^7$ substituents wherein each $R^7$ is independently halogen, $C_{1-3}$alkyl, $-(CH_2)_t-F_q$, $-CF_3$, $-(CH_2)_t-C_{3-4}$cycloalkyl, or $-(CH_2)_t-O-C_{1-3}$alkyl. In any of the embodiments described above, $R^4$ is a 5- to 10-membered heteroaryl with 3 heteroatoms and is optionally substituted with 1 to 3 $R^7$ substituents wherein each $R^7$ is independently halogen, $C_{1-3}$alkyl, $-(CH_2)_t-F_q$, $-CF_3$, $-(CH_2)_t-C_{3-4}$ cycloalkyl, or $-(CH_2)_t-O-C_{1-3}$alkyl. In any of the embodiments described above, $R^4$ is an isoxazole optionally substituted with 1 to 2 $R^7$ substituents, wherein t is zero. In any of the embodiments described above, $R^4$ is a thiazole optionally substituted with 1 to 2 $R^7$ substituents, wherein t is zero. In any of the embodiments described above, $R^4$ is a pyrimidine optionally substituted with 1 to 3 $R^7$ substituents, wherein t is zero. In any of the embodiments described above, $R^4$ is an isothiazole optionally substituted with 1 to 2 $R^7$ substituents, wherein t is zero. In any of the embodiments described above, $R^4$ is a pyridine optionally substituted with 1 to 3 $R^7$ substituents, wherein t is zero. In any of the embodiments described above, $R^4$ is a pyrazole optionally substituted with 1 to 3 $R^7$ substituents, wherein t is zero.

In any of the embodiments described above, $R^3$ is hydrogen or $C_{1-3}$alkyl. In any of the embodiments described above, $R^3$ is hydrogen. In any of the embodiments described above, $R^3$ is $C_{1-3}$alkyl. In any of the embodiments described above, $R^3$ is methyl.

It is understood that descriptions of any one substituent, such as $R^1$, may be combined with descriptions of any other substituents, such as $R^2$, such that each and every combination of the first substituent and the second substituent is provided herein the same as if each combination were specifically and individually listed. For example, in one variation, $R^1$ is taken together with $R^2$ to provide an embodiment wherein $R^1$ is methyl and $R^2$ is fluorine.

It will be understood that the compounds of formula I and Ia, and pharmaceutically acceptable salts thereof, also include hydrates, solvates and polymorphs of said compounds of formula I and Ia, and pharmaceutically acceptable salts thereof, as discussed below.

In one embodiment, the invention also relates to each of the individual compounds described as Examples 1-44 in the Examples section of the subject application, (including the free bases or pharmaceutically acceptable salts thereof).

In another embodiment the invention relates to a compound selected from the group consisting of:
4-{1-[1-(1,3-benzothiazol-2-ylmethyl)piperidin-4-yl]-4-(4-fluorophenyl)-1H-imidazol-5-yl}pyrimidin-2-amine
4-[4-(4-fluorophenyl)-1-{1-[(5-methylisoxazol-3-yl)methyl]piperidin-4-yl}-1H-imidazol-5-yl]pyrimidin-2-amine
4-{4-(4-fluorophenyl)-1-[1-(1,3-thiazol-2-ylmethyl)piperidin-4-yl]-1H-imidazol-5-yl}pyrimidin-2-amine
4-[4-(4-fluorophenyl)-1-{1-[(4-isopropyl-1,3-thiazol-2-yl)methyl]piperidin-4-yl}-1H-imidazol-5-yl]pyrimidin-2-amine
4-[1-{1-[(5-ethylisoxazol-3-yl)methyl]pyrrolidin-3-yl}-4-(4-fluorophenyl)-1H-imidazol-5-yl]pyrimidin-2-amine
4-{4-(4-fluorophenyl)-1-[1-(pyridin-3-ylmethyl)pyrrolidin-3-yl]-1H-imidazol-5-yl}pyrimidin-2-amine
4-{4-(4-fluorophenyl)-1-[1-(pyridin-2-ylmethyl)pyrrolidin-3-yl]-1H-imidazol-5-yl}pyrimidin-2-amine
4-[4-(4-fluorophenyl)-1-{1-[(2-methyl-1,3-thiazol-4-yl)methyl]pyrrolidin-3-yl}-1H-imidazol-5-yl]pyrimidin-2-amine
4-[1-{1-[(2-cyclopropylpyrimidin-4-yl)methyl]pyrrolidin-3-yl}-4-(4-fluorophenyl)-1H-imidazol-5-yl]pyrimidin-2-amine
4-{4-(4-fluorophenyl)-1-[1-(isoquinolin-5-ylmethyl)pyrrolidin-3-yl]-1H-imidazol-5-yl}pyrimidin-2-amine
4-{4-(4-fluorophenyl)-1-[1-(1,3-thiazol-5-ylmethyl)pyrrolidin-3-yl]-1H-imidazol-5-yl}pyrimidin-2-amine
4-[4-(4-fluorophenyl)-1-{1-[(5-methylpyridin-2-yl)methyl]pyrrolidin-3-yl}-1H-imidazol-5-yl]pyrimidin-2-amine
4-{4-(4-fluorophenyl)-1-[1-(quinoxalin-5-ylmethyl)pyrrolidin-3-yl]-1H-imidazol-5-yl}pyrimidin-2-amine
4-{4-(4-fluorophenyl)-1-[1-(quinoxalin-2-ylmethyl)pyrrolidin-3-yl]-1H-imidazol-5-yl}pyrimidin-2-amine
4-[4-(4-fluorophenyl)-1-{1-[(6-methylpyridin-3-yl)methyl]pyrrolidin-3-yl}-1H-imidazol-5-yl]pyrimidin-2-amine
4-[4-(4-fluorophenyl)-1-(1-{[6-(trifluoromethyl)pyridin-3-yl]methyl}pyrrolidin-3-yl)-1H-imidazol-5-yl]pyrimidin-2-amine
4-{4-(4-fluorophenyl)-1-[1-(1,3-thiazol-2-ylmethyl)pyrrolidin-3-yl]-1H-imidazol-5-yl}pyrimidin-2-amine
4-[1-{1-[(1,5-dimethyl-1H-pyrazol-4-yl)methyl]pyrrolidin-3-yl}-4-(4-fluorophenyl)-1H-imidazol-5-yl]pyrimidine
4-[4-(4-fluorophenyl)-1-{1-[(6-methylpyridin-2-yl)methyl]pyrrolidin-3-yl}-1H-imidazol-5-yl]pyrimidine
4-[4-(4-fluorophenyl)-1-{1-[(1-methyl-1H-pyrazol-4-yl)methyl]pyrrolidin-3-yl}-1H-imidazol-5-yl]pyrimidine
6-({3-[4-(4-fluorophenyl)-5-pyrimidin-4-yl-1H-imidazol-1-yl]pyrrolidin-1-yl}methyl)quinoxaline
4-[4-(4-fluorophenyl)-1-{1-[(5-methylpyrazin-2-yl)methyl]pyrrolidin-3-yl}-1H-imidazol-5-yl]pyrimidine
4-{4-(4-fluorophenyl)-1-[1-(pyridin-4-ylmethyl)pyrrolidin-3-yl]-1H-imidazol-5-yl}pyrimidine
4-[4-(4-fluorophenyl)-1-{1-[(5-methylisoxazol-3-yl)methyl]pyrrolidin-3-yl}-1H-imidazol-5-yl]pyrimidine
4-{4-(4-fluorophenyl)-1-[1-(pyridin-3-ylmethyl)pyrrolidin-3-yl]-1H-imidazol-5-yl}pyrimidine
4-[1-{1-[(6-ethoxypyridin-3-yl)methyl]pyrrolidin-3-yl}-4-(4-fluorophenyl)-1H-imidazol-5-yl]pyrimidine
4-[1-{1-[(5-ethylisoxazol-3-yl)methyl]pyrrolidin-3-yl}-4-(4-fluorophenyl)-1H-imidazol-5-yl]pyrimidine
4-{4-(4-fluorophenyl)-1-[1-(1H-pyrazol-3-ylmethyl)pyrrolidin-3-yl]-1H-imidazol-5-yl}pyrimidine
4-{4-(4-fluorophenyl)-1-[1-(pyridin-2-ylmethyl)pyrrolidin-3-yl]-1H-imidazol-5-yl}pyrimidine
4-[4-(4-fluorophenyl)-1-{1-[(1-propyl-1H-pyrazol-4-yl)methyl]pyrrolidin-3-yl}-1H-imidazol-5-yl]pyrimidine
2-cyclopropyl-4-({3-[4-(4-fluorophenyl)-5-pyrimidin-4-yl-1H-imidazol-1-yl]pyrrolidin-1-yl}methyl)pyrimidine
4-({3-[4-(4-fluorophenyl)-5-pyrimidin-4-yl-1H-imidazol-1-yl]pyrrolidin-1-yl}methyl)pyridine-2-carbonitrile
4-[4-(4-fluorophenyl)-1-{1-[(1-methyl-1H-pyrazol-3-yl)methyl]pyrrolidin-3-yl}-1H-imidazol-5-yl]pyrimidine
4-[4-(4-fluorophenyl)-1-{1-[(6-methoxypyridin-3-yl)methyl]pyrrolidin-3-yl}-1H-imidazol-5-yl]pyrimidine
4-({3-[4-(4-fluorophenyl)-5-pyrimidin-4-yl-1H-imidazol-1-yl]pyrrolidin-1-yl}methyl)-2-methylpyrimidine
4-[4-(4-fluorophenyl)-1-{1-[(5-methylpyridin-2-yl)methyl]pyrrolidin-3-yl}-1H-imidazol-5-yl]pyrimidine
5-({3-[4-(4-fluorophenyl)-5-pyrimidin-4-yl-1H-imidazol-1-yl]pyrrolidin-1-yl}methyl)quinoxaline
4-({3-[4-(4-fluorophenyl)-5-pyrimidin-4-yl-1H-imidazol-1-yl]pyrrolidin-1-yl}methyl)pyrimidine
4-{4-(4-fluorophenyl)-1-[1-(1,3-thiazol-5-ylmethyl)pyrrolidin-3-yl]-1H-imidazol-5-yl}pyrimidine 4-[4-(4-fluorophenyl)-1-{1-[(2-methoxypyridin-4-yl)methyl]pyrrolidin-3-yl}-1H-imidazol-5-yl]pyrimidine 2-({3-[4-(4-fluorophenyl)-5-pyrimidin-4-yl-1H-imidazol-1-yl]pyrrolidin-1-yl}methyl)quinoxaline 4-[4-(4-fluorophenyl)-1-{1-[(1-methyl-1H-pyrazol-5-yl)methyl]pyrrolidin-3-yl}-1H-imidazol-5-yl]pyrimidine 5-({3-[4-(4-fluorophenyl)-5-pyrimidin-4-yl-1H-imidazol-1-yl]pyrrolidin-1-yl}methyl)-2-methylpyrimidine 4-[4-(4-fluorophenyl)-1-{1-[(2-methoxypyridin-3-yl)methyl]pyrrolidin-3-yl}-1H-imidazol-5-yl]pyrimidine 4-[4-(4-fluorophenyl)-1-{1-[(5-methoxy-1,3-dimethyl-1H-pyrazol-4-yl)methyl]pyrrolidin-3-yl}-1H-imidazol-5-yl]pyrimidine 4-[4-(4-fluorophenyl)-1-{1-[(1-isopropyl-1H-pyrazol-4-yl)methyl]pyrrolidin-3-yl}-1H-imidazol-5-yl]pyrimidine 4-[4-(4-fluorophenyl)-1-{1-[(2-methylpyridin-4-yl)methyl]pyrrolidin-3-yl}-1H-imidazol-5-yl]pyrimidine 4-[4-(4-fluorophenyl)-1-{1-[(2-methyl-1,3-thiazol-5-yl)methyl]pyrrolidin-3-yl}-1H-imidazol-5-yl]pyrimidine 4-[1-{1-[(1,3-dimethyl-1H-pyrazol-4-yl)methyl]pyrrolidin-3-yl}-4-(4-fluorophenyl)-1H-imidazol-5-yl]pyrimidine 4-[4-(4-fluorophenyl)-1-{1-[(6-methylpyridin-3-yl)methyl]pyrrolidin-3-yl}-1H-imidazol-5-yl]pyrimidine 4-[1-{1-[(1-ethyl-5-methyl-1H-pyrazol-4-yl)methyl]pyrrolidin-3-yl}-4-(4-fluorophenyl)-1H-imidazol-5-yl]pyrimidine 4-[1-{1-[(1-ethyl-1H-pyrazol-4-yl)methyl]pyrrolidin-3-yl}-4-(4-fluorophenyl)-1H-imidazol-5-yl]pyrimidine 5-({3-[4-(4-fluorophenyl)-5-pyrimidin-4-yl-1H-imidazol-1-yl]pyrrolidin-1-yl}methyl)-2-propylpyrimidine 4-{4-(4-fluorophenyl)-1-[1-(quinoxalin-6-ylmethyl)azetidin-3-yl]-1H-imidazol-5-yl}pyrimidin-2-amine 4-[4-(4-fluorophenyl)-1-{1-[(2-methoxypyridin-3-yl)methyl]azetidin-3-yl}-1H-imidazol-5-yl]pyrimidin-2-amine 4-[4-(4-fluorophenyl)-1-{1-[(5-methylpyridin-2-yl)methyl]azetidin-3-yl}-1H-imidazol-5-yl]pyrimidin-2-amine 4-[4-(4-fluorophenyl)-1-{1-[(2-methoxypyridin-4-yl)methyl]azetidin-3-yl}-1H-imidazol-5-yl]pyrimidin-2-amine 4-[4-(4-fluorophenyl)-1-{1-[(6-methoxypyridin-3-yl)methyl]azetidin-3-yl}-1H-imidazol-5-yl]pyrimidin-2-amine 4-{4-(4-fluorophenyl)-1-[1-(quinoxalin-5-ylmethyl)azetidin-3-yl]-1H-imidazol-5-yl}pyrimidin-2-amine 4-[4-(4-fluorophenyl)-1-{1-[(5-methyl-2-furyl)methyl]azetidin-3-yl}-1H-imidazol-5-yl]pyrimidin-2-amine 4-({4-[4-(4-fluorophenyl)-5-pyrimidin-4-yl-1H-imidazol-1-yl]piperidin-1-yl}methyl)pyrimidine 4-{4-(4-fluorophenyl)-1-[1-(1,3-oxazol-4-ylmethyl)piperidin-4-yl]-1H-imidazol-5-yl}pyrimidine 4-{4-(4-fluorophenyl)-1-[1-(pyrimidin-5-ylmethyl)piperidin-4-yl]-1H-imidazol-5-yl}pyrimidine 2-cyclopropyl-4-({4-[4-(4-fluorophenyl)-5-pyrimidin-4-yl-1H-imidazol-1-yl]piperidin-1-yl}methyl)pyrimidine 4-({4-[4-(4-fluorophenyl)-5-pyrimidin-4-yl-1H-imidazol-1-yl]piperidin-1-yl}methyl)-2-methylpyrimidine 4-{4-(4-fluorophenyl)-1-[1-(isoxazol-3-ylmethyl)-2-methylpiperidin-4-yl]-1H-imidazol-5-yl}pyrimidin-2-amine 4-{4-(4-fluorophenyl)-1-[1-(isoxazol-3-ylmethyl)-3-methylpiperidin-4-yl]-1H-imidazol-5-yl}pyrimidin-2-amine 4-{4-(4-fluorophenyl)-1-[1-(isoxazol-3-ylmethyl)-4-methylpiperidin-4-yl]-1H-imidazol-5-yl}pyrimidin-2-amine 4-{4-(4-fluorophenyl)-1-[1-(isoxazol-3-ylmethyl)-2-methylpiperidin-4-yl]-1H-imidazol-5-yl}pyrimidine 4-{4-(4-fluorophenyl)-1-[1-(isoxazol-3-ylmethyl)-3-methylpiperidin-4-yl]-1H-imidazol-5-yl}pyrimidine 4-{4-(4-fluorophenyl)-1-[1-(isoxazol-3-ylmethyl)-4-methylpiperidin-4-yl]-1H-imidazol-5-yl}pyrimidine 4-{4-(4-fluorophenyl)-1-[1-(isoxazol-3-ylmethyl)-2-methylpyrrolidin-3-yl]-1H-imidazol-5-yl}pyrimidin-2-amine 4-{4-(4-fluorophenyl)-1-[1-(isoxazol-3-ylmethyl)-4-methylpyrrolidin-3-yl]-1H-imidazol-5-yl}pyrimidin-2-amine 4-{4-(4-fluorophenyl)-1-[1-(isoxazol-3-ylmethyl)-3-methylpyrrolidin-3-yl]-1H-imidazol-5-yl}pyrimidin-2-amine 4-{4-(4-fluorophenyl)-1-[1-(isoxazol-3-ylmethyl)-2-methylpyrrolidin-3-yl]-1H-imidazol-5-yl}pyrimidine 4-{4-(4-fluorophenyl)-1-[1-(isoxazol-3-ylmethyl)-4-methylpyrrolidin-3-yl]-1H-imidazol-5-yl}pyrimidine 4-{4-(4-fluorophenyl)-1-[1-(isoxazol-3-ylmethyl)-3-methylpyrrolidin-3-yl]-1H-imidazol-5-yl}pyrimidine 4-{4-(4-fluorophenyl)-1-[1-(isoxazol-3-ylmethyl)piperidin-4-yl]-1H-imidazol-5-yl}pyridin-2-amine and the pharmaceutically acceptable salts of each of the foregoing.

In another embodiment, the invention relates to methods for inhibiting casein kinase 1 CK1 delta or CK1 epsilon activity in a patient comprising the administration of a therapeutically effective amount of an inhibitor of casein kinase 1 CK1 delta or CK1 epsilon.

In another embodiment, the invention relates to methods of inhibiting casein kinase CK1 delta or CK1 epsilon activity which result in a lengthening of the circadian rhythm period.

In another embodiment, the invention relates to a method of treating a mood disorder or a sleep disorder comprising the administration of a therapeutically effective amount of an inhibitor of casein kinase1 CK1 delta or CK1 epsilon. In one embodiment, the invention relates to a method of treating a sleep disorder. In a further embodiment, the sleep disorder is a circadian rhythm sleep disorder. In yet another embodiment, the circadian rhythm sleep disorder is selected from the group consisting of shift work sleep disorder, jet lag syndrome, advanced sleep phase syndrome and delayed sleep phase syndrome.

In a further embodiment, the invention relates to a method of treating a mood disorder selected from the group consisting of a depressive disorder and a bipolar disorder. In another embodiment of the invention, the depressive disorder is major depressive disorder. In a further embodiment of the invention, the mood disorder is a bipolar disorder. In another embodiment, the bipolar disorder is selected from the group consisting of bipolar I disorder and bipolar II disorder.

In another embodiment the present invention provides methods of treating neurological and psychiatric disorders comprising: administering to a mammal an amount of a compound of formula I effective in treating such disorders, or a pharmaceutically acceptable salt thereof. Neurological and psychiatric disorders include but are not limited to: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia, AIDS-induced dementia, vascular dementia, mixed dementias, age-associated memory impairment, Alzheimer's disease, Huntington's Chorea, amyotrophic lateral sclerosis, ocular damage, retinopathy, cognitive disorders, including cognitive disorders associated with schizophrenia and bipolar disorders, idiopathic and drug-induced Parkinson's disease, muscular spasms and disorders associated with muscular spasticity including tremors, epilepsy, convulsions, migraine, migraine headache, urinary incontinence, substance tolerance, substance withdrawal, withdrawal from opiates, nicotine, tobacco products, alcohol, benzodiazepines, cocaine, sedatives, and hypnotics, psychosis, mild cognitive impairment, amnestic cognitive impairment, multi-domain cognitive impairment, obesity, schizophrenia, anxiety, generalized anxiety disorder, social anxiety disorder, panic disorder, post-traumatic stress disorder, obsessive compulsive disorder, mood disorders, depression, mania, bipolar disorders, trigeminal neuralgia, hearing loss, tinnitus, macular degeneration of the eye, emesis, brain edema, pain, acute and chronic pain states, severe pain, intractable pain, neuropathic pain, post-traumatic pain, tardive dyskinesia, sleep disorders, narcolepsy, attention deficit/hyperactivity disorder, autism, Asperger's disease, and conduct disorder in a mammal. Accordingly, in one embodiment, the invention provides a method for treating a condition in a mammal, such as a human, selected from the conditions above, comprising administering a compound of formula I to the mammal. The mammal is preferably a mammal in need of such treatment.

As examples, the invention provides a method for treating attention deficit/hyperactivity disorder, schizophrenia and Alzheimer's Disease.

In another embodiment the present invention provides methods of treating neurological and psychiatric disorders comprising: administering to a patient in need thereof an amount of a compound of formula I effective in treating such disorders. The compound of formula I is optionally used in combination with another active agent. Such an active agent may be, for example, an atypical antipsychotic, a cholinesterase inhibitor, Dimebon, or NMDA receptor antagonist. Such atypical antipsychotics include, but are not limited to, ziprasidone, clozapine, olanzapine, risperidone, quetiapine, aripiprazole, paliperidone; such NMDA receptor antagonists include but are not limited to memantine; and such cholinesterase inhibitors include but are not limited to donepezil and galantamine.

The invention is also directed to a pharmaceutical composition comprising a compound of formula I, and a pharmaceutically acceptable carrier. The composition may be, for example, a composition for treating a condition selected from the group consisting of neurological and psychiatric disorders, including but not limited to: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia, AIDS-induced dementia, vascular dementia, mixed dementias, age-associated memory impairment, Alzheimer's disease, Huntington's Chorea, amyotrophic lateral sclerosis, ocular damage, retinopathy, cognitive disorders, including cognitive disorders associated with schizophrenia and bipolar disorders, idiopathic and drug-induced Parkinson's disease, muscular spasms and disorders associated with muscular spasticity including tremors, epilepsy, convulsions, migraine, migraine headache, urinary incontinence, substance tolerance, substance withdrawal, withdrawal from opiates, nicotine, tobacco products, alcohol, benzodiazepines, cocaine, sedatives, and hypnotics, psychosis, mild cognitive impairment, amnestic cognitive impairment, multi-domain cognitive impairment, obesity, schizophrenia, anxiety, generalized anxiety disorder, social anxiety disorder, panic disorder, post-traumatic stress disorder, obsessive compulsive disorder, mood disorders, depression, mania, bipolar disorders, trigeminal neuralgia, hearing loss, tinnitus, macular degeneration of the eye, emesis, brain edema, pain, acute and chronic pain states, severe pain, intractable pain, neuropathic pain, post-traumatic pain, tardive dyskinesia, sleep disorders, narcolepsy, attention deficit/hyperactivity disorder, autism, Asperger's disease, and conduct disorder in a mammal, comprising administering an effective amount of a compound of formula 1 or pharmaceutically acceptable salt thereof, and a pharmaceutically acceptable carrier. The composition optionally further comprises an atypical antipsychotic, a cholinesterase inhibitor, Dimebon, or NMDA receptor antagonist. Such atypical antipsychotics include, but are not limited to, ziprasidone, clozapine, olanzapine, risperidone, quetiapine, aripiprazole, paliperidone; such NMDA receptor antagonists include but are not limited to memantine; and such cholinesterase inhibitors include but are not limited to donepezil and galantamine.

The compounds of the present invention are also adapted to therapeutic use as antiproliferative agents (e.g., cancer), antitumor (e.g., effect against solid tumors) in mammals, particularly in humans. In particular, the compounds of the present invention are useful in the prevention and treatment of a variety of human hyperproliferative disorders including both malignant and benign abnormal cell growth.

The compounds, compositions and methods provided herein are useful for the treatment of cancer including but are not limited to:

circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue;

respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

gastrointestinal, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma);

bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs;

hematologic, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx;

skin, for example, malignant melanoma, cutaneous melanoma, basal cell carcinoma, squamous cell carcinoma, Karposi's sarcoma, moles dysplastic nevi, lipoma, angioma, dermatofibroma, and keloids;

adrenal glands: neuroblastoma; and cancers involving other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of "cancer" when used herein in connection with the present invention include cancer selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, or a combination of one or more of the foregoing cancers.

Still more specifically, examples of "cancer" when used herein in connection with the present invention include cancer selected from lung cancer (NSCLC and SCLC), breast cancer, ovarian cancer, colon cancer, rectal cancer, cancer of the anal region, or a combination of one or more of the foregoing cancers.

In one embodiment of the present invention the non-cancerous conditions include such hyperplastic conditions such as benign hyperplasia of the skin (e.g., psoriasis) and benign hyperplasia of the prostate (e.g., BPH).

As noted above, the compounds of the invention may be used in combination with one or more additional anti-cancer agents which are described below. When a combination therapy is used, the one or more additional anti-cancer agents may be administered sequentially or simultaneously with the compound of the invention. In one embodiment, the additional anti-cancer agent is administered to a mammal (e.g., a human) prior to administration of the compound of the invention. In another embodiment, the additional anti-cancer agent is administered to the mammal after administration of the compound of the invention. In another embodiment, the additional anti-cancer agent is administered to the mammal (e.g., a human) simultaneously with the administration of the compound of the invention.

The invention also relates to a pharmaceutical composition for the treatment of abnormal cell growth in a mammal, including a human, which comprises an amount of a compound of Formula I, as defined above (including hydrates, solvates and polymorphs of said compound or pharmaceutically acceptable salts thereof), in combination with one or more (preferably one to three) anti-cancer agents selected from the group consisting of anti-angiogenesis agents and signal transduction inhibitors and a pharmaceutically acceptable carrier, wherein the amounts of the active agent and the combination anti-cancer agents when taken as a whole is therapeutically effective for treating said abnormal cell growth.

DEFINITIONS

The term "alkyl" refers to a linear or branched-chain saturated hydrocarbyl substituent (i.e., a substituent obtained from a hydrocarbon by removal of a hydrogen) containing from one to twenty carbon atoms; in one embodiment from one to twelve carbon atoms; in another embodiment, from one to ten carbon atoms; in another embodiment, from one to six carbon atoms; and in another embodiment, from one to four carbon atoms. Examples of such substituents include methyl, ethyl, propyl (including n-propyl and isopropyl), butyl (including n-butyl, isobutyl, sec-butyl and tert-butyl), pentyl, isoamyl, hexyl and the like. In some instances, the number of carbon atoms in a hydrocarbyl substituent (i.e., alkyl, alkenyl, cycloalkyl, aryl, etc.) is indicated by the prefix "$C_{x-y}$," wherein x is the minimum and y is the maximum number of carbon atoms in the substituent. Thus, for example, "$C_{1-6}$alkyl" refers to an alkyl substituent containing from 1 to 6 carbon atoms.

"Alkenyl" refers to an aliphatic hydrocarbon having at least one carbon-carbon double bond, including straight chain, branched chain or cyclic groups having at least one carbon-carbon double bond. Preferably, it is a medium size alkenyl having 2 to 6 carbon atoms. For example, as used herein, the term "$C_{2-6}$ alkenyl" means straight or branched chain unsaturated radicals of 2 to 6 carbon atoms, including, but not limited to ethenyl, 1-propenyl, 2-propenyl (allyl), isopropenyl, 2-methyl-1-propenyl, 1-butenyl, 2-butenyl, and the like; optionally substituted by 1 to 5 suitable substituents as defined above such as fluoro, chloro, trifluoromethyl, ($C_1$-$C_6$) alkoxy, ($C_6$-$C_{10}$)aryloxy, trifluoromethoxy, difluoromethoxy or $C_1$-$C_6$alkyl. When the compounds of the invention contain a $C_{2-6}$alkenyl group, the compound may exist as the pure E (entgegen) form, the pure Z (zusammen) form, or any mixture thereof.

"Alkynyl" refers to an aliphatic hydrocarbon having at least one carbon-carbon triple bond, including straight chain, branched chain or cyclic groups having at least one carbon-carbon triple bond. Preferably, it is a lower alkynyl having 2 to 6 carbon atoms. For example, as used herein, the term "$C_{2-6}$alkynyl" is used herein to mean a straight or branched hydrocarbon chain alkynyl radical as defined above having 2 to 6 carbon atoms and one triple bond.

The term "cycloalkyl" refers to a carbocyclic substituent obtained by removing a hydrogen from a saturated carbocyclic molecule and having three to fourteen carbon atoms. In one embodiment, a cycloalkyl substituent has three to ten carbon atoms. Examples of cycloalkyl include cyclopropyl, cyclobutyl, cyclopentyl and cyclohexyl.

The term "cycloalkyl" also includes substituents that are fused to a $C_6$-$C_{10}$ aromatic ring or to a 5- to 10-membered heteroaromatic ring, wherein a group having such a fused cycloalkyl group as a substituent is bound to a carbon atom of the cycloalkyl group. When such a fused cycloalkyl group is substituted with one or more substituents, the one or more substituents, unless otherwise specified, are each bound to a carbon atom of the cycloalkyl group. The fused $C_6$-$C_{10}$ aromatic ring or 5-10-membered heteroaromatic ring may be optionally substituted with halogen, $C_{1-6}$alkyl, $C_{3-10}$cycloalkyl, or =O.

A cycloalkyl may be a single ring, which typically contains from 3 to 6 ring atoms. Examples include cyclopropyl, cyclobutyl, cyclopentyl, and cyclohexyl. Alternatively, 2 or 3 rings may be fused together, such as bicyclodecanyl and decalinyl.

The term "aryl" refers to an aromatic substituent containing one ring or two or three fused rings. The aryl substituent may have six to eighteen carbon atoms. As an example, the aryl substituent may have six to fourteen carbon atoms. The term "aryl" may refer to substituents such as phenyl, naphthyl and anthracenyl. The term "aryl" also includes substituents such as phenyl, naphthyl and anthracenyl that are fused to a $C_{4-10}$ carbocyclic ring, such as a $C_5$ or a $C_6$ carbocyclic ring, or to a 4- to 10-membered heterocyclic ring, wherein a group having such a fused aryl group as a substituent is bound to an aromatic carbon of the aryl group. When such a fused aryl group is substituted with one more substituents, the one or more substituents, unless otherwise specified, are each bound to an aromatic carbon of the fused aryl group. The fused $C_{4-10}$ carbocyclic or 4- to 10-membered heterocyclic ring may be optionally substituted with halogen, $C_{1-6}$alkyl, $C_{3-10}$cycloalkyl, or =O. Examples of aryl groups include accordingly phenyl, naphthalenyl, tetrahydronaphthalenyl (also known as "tetralinyl"), indenyl, isoindenyl, indanyl, anthracenyl, phenanthrenyl, benzonaphthenyl (also known as "phenalenyl"), and fluorenyl.

In some instances, the number of atoms in a cyclic substituent containing one or more heteroatoms (i.e., heteroaryl or heterocycloalkyl) is indicated by the prefix "X-Y-membered", wherein wherein x is the minimum and y is the maximum number of atoms forming the cyclic moiety of the substituent. Thus, for example, 5- to 8-membered heterocycloalkyl refers to a heterocycloalkyl containing from 5 to 8 atoms, including one or more heteroatoms, in the cyclic moiety of the heterocycloalkyl.

The term "hydrogen" refers to a hydrogen substituent, and may be depicted as —H.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents are attached include, for example, alcohols, enols and phenol.

The term "cyano" (also referred to as "nitrile") means —CN, which also may be depicted:

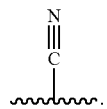 [SMILES: *C#N]

The term "halogen" refers to fluorine (which may be depicted as —F), chlorine (which may be depicted as —Cl), bromine (which may be depicted as —Br), or iodine (which may be depicted as —I). In one embodiment, the halogen is chlorine. In another embodiment, the halogen is fluorine. In another embodiment, the halogen is bromine.

The term "heterocycloalkyl" refers to a substituent obtained by removing a hydrogen from a saturated or partially saturated ring structure containing a total of 4 to 14 ring atoms, wherein at least one of the ring atoms is a heteroatom selected from oxygen, nitrogen, or sulfur. For example, as used herein, the term "4- to 10-membered heterocycloalkyl" means the substituent is a single ring with 4 to 10 total members. A heterocycloalkyl alternatively may comprise 2 or 3 rings fused together, wherein at least one such ring contains a heteroatom as a ring atom (i.e., nitrogen, oxygen, or sulfur). In a group that has a heterocycloalkyl substituent, the ring atom of the heterocycloalkyl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heterocycloalkyl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom.

The term "heterocycloalkyl" also includes substituents that are fused to a $C_{6-10}$ aromatic ring or to a 5- to 10-membered heteroaromatic ring, wherein a group having such a fused heterocycloalkyl group as a substituent is bound to a heteroatom of the heterocycloalkyl group or to a carbon atom of the heterocycloalkyl group. When such a fused heterocycloalkyl group is substituted with one or more substituents, the one or more substituents, unless otherwise specified, are each bound to a heteroatom of the heterocycloalkyl group or to a carbon atom of the heterocycloalkyl group. The fused $C_6$-$C_{10}$ aromatic ring or 5- to 10-membered heteroaromatic ring may be optionally substituted with halogen, $C_{1-6}$ alkyl, $C_{3-10}$cycloalkyl, $C_{1-6}$alkoxy, or =O.

The term "heteroaryl" refers to an aromatic ring structure containing from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A heteroaryl may be a single ring or 2 or 3 fused rings. Examples of heteroaryl substituents include but are not limited to: 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2, 5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused ring substituents such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridyl N-oxides and groups containing a pyridine N-oxide ring.

Examples of single-ring heteroaryls and heterocycloalkyls include but are not limited to furanyl, dihydrofuranyl, tetrahydrofuranyl, thiophenyl (also known as "thiofuranyl"), dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, isoxazolinyl, thiazolyl, isothiazolyl, thiazolinyl, isothiazolinyl, thiazolidinyl, isothiazolidinyl, thiadiazolyl, oxathiazolyl, oxadiazolyl (including oxadiazolyl, 1,2,4-oxadiazolyl (also known as "azoximyl"), 1,2,5-oxadiazolyl (also known as "furazanyl"), or 1,3,4-oxadiazolyl), pyranyl (including 1,2-pyranyl or 1,4-pyranyl), dihydropyranyl, pyridinyl (also known as "azinyl"), piperidinyl, diazinyl (including pyridazinyl (also known as "1,2-diazinyl"), pyrimidinyl (also known as "1,3-diazinyl" or "pyrimidyl"), or pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl")), morpholinyl, azepinyl, oxepinyl, thiepinyl, and diazepinyl.

Examples of 2-fused-ring heteroaryls include but are not limited to indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl, indolyl, isoindolyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl.

Examples of 3-fused-ring heteroaryls or heterocycloalkyls include but are not limited to 5,6-dihydro-4H-imidazo[4,5,1-ij]quinoline, 4,5-dihydroimidazo[4,5,1-hi]indole, 4,5,6,7-tetrahydroimidazo[4,5,1-jk][1]benzazepine, and dibenzofuranyl.

Other examples of fused-ring heteroaryls include but are not limited to benzo-fused heteroaryls such as indolyl, isoindolyl (also known as "isobenzazolyl" or "pseudoisoindolyl"), indoleninyl (also known as "pseudoindolyl"), isoindazolyl (also known as "benzpyrazolyl"), benzazinyl (including quinolinyl (also known as "1-benzazinyl") or isoquinolinyl (also known as "2-benzazinyl")), phthalazinyl, quinoxalinyl, quinazolinyl, benzodiazinyl (including cinnolinyl (also known as "1,2-benzodiazinyl") or quinazolinyl (also known as "1,3-benzodiazinyl")), benzopyranyl (including "chromanyl" or "isochromanyl"), benzothiopyranyl (also known as "thiochromanyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl," "thionaphthenyl," or "benzothiofuranyl"), isobenzothienyl (also known as "isobenzothiophenyl," "isothionaphthenyl," or "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, or 3,1,4-benzoxazinyl), benzisoxazinyl (including 1,2-benzisoxazinyl or 1,4-benzisoxazinyl), tetrahydroisoquinolinyl, carbazolyl, xanthenyl, and acridinyl.

The term "heteroaryl" also includes substituents such as pyridyl and quinolinyl that are fused to a $C_{4-10}$ carbocyclic ring, such as a $C_5$ or a $C_6$ carbocyclic ring, or to a 4-10-membered heterocyclic ring, wherein a group having such a fused heteroaryl group as a substituent is bound to an aromatic carbon of the heteroaryl group or to a heteroatom of the heteroaryl group. When such a fused heteroaryl group is substituted with one or more substituents, the one or more substitutents, unless otherwise specified, are each bound to an aromatic carbon of the heteroaryl group or to a heteroatom of the heteroaryl group. The fused $C_{4-10}$ carbocyclic or 4-10-membered heterocyclic ring may be optionally substituted with halogen, $C_{1-6}$ alkyl, $C_{3-10}$ cycloalkyl, or =O.

Additional examples of heteroaryls and heterocycloalkyls include but are not limited to: 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzo[1,3]dioxine, benzo[1,4]dioxine, benzopyrrolidinyl, benzopiperidinyl, benzoxolanyl, benzothiolanyl, 4,5,6,7-tetrahydropyrazol[1,5-a]pyridine, benzothianyl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-2-yl (C-attached).

A substituent is "substitutable" if it comprises at least one carbon or nitrogen atom that is bonded to one or more hydrogen atoms. Thus, for example, hydrogen, halogen, and cyano do not fall within this definition.

If a substituent is described as being "substituted," a non-hydrogen substituent is in the place of a hydrogen substituent on a carbon or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R", wherein R' and R" together with the nitrogen atom to which they are attached may form a heterocyclic ring comprising 1 or 2 heteroatoms independently selected from oxygen, nitrogen, or sulfur, wherein said heterocycloalkyl moiety may be optionally substituted. The heterocyclic ring formed from R' and R" together with the nitrogen atom to which they are attached may be partially or fully saturated, or aromatic. In one embodiment, the heterocyclic ring consists of 4 to 10 atoms. In another embodiment, the heterocyclic ring is selected from the group consisting of piperidinyl, morpholinyl, azetidinyl, pyrrolyl, imidazolyl, pyrazolyl, triazolyl, tetrazolyl, isoxazolyl and thiazolyl.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent. To illustrate further, if an amino nitrogen is described as being optionally substituted with up to 2 non-hydrogen substituents, then the nitrogen will be optionally substituted with up to 2 non-hydrogen substituents if the amino nitrogen is a primary nitrogen, whereas the amino nitrogen will be optionally substituted with up to only 1 non-hydrogen substituent if the amino nitrogen is a secondary nitrogen.

A prefix attached to a multi-moiety substituent only applies to the first moiety. To illustrate, the term "alkylcycloalkyl" contains two moieties: alkyl and cycloalkyl. Thus, a $C_{1-6}$-prefix on $C_{1-6}$alkylcycloalkyl means that the alkyl moiety of the alkylcycloalkyl contains from 1 to 6 carbon atoms; the $C_{1-6}$-prefix does not describe the cycloalkyl moiety. To illustrate further, the prefix "halo" on haloalkoxyalkyl indicates that only the alkoxy moiety of the alkoxyalkyl substituent is substituted with one or more halogen substituents. If the halogen substitution only occurs on the alkyl moiety, the substituent would be described as "alkoxyhaloalkyl." If the halogen substitution occurs on both the alkyl moiety and the alkoxy moiety, the substituent would be described as "haloalkoxyhaloalkyl."

If substituents are described as being "independently selected" from a group, each substituent is selected independent of the other(s). Each substituent therefore may be identical to or different from the other substituent(s).

As used herein the term "Formula I" may be hereinafter referred to as a "compound(s) of the invention." Such terms are also defined to include all forms of the compound of Formula I, including hydrates, solvates, isomers, crystalline and non-crystalline forms, isomorphs, polymorphs, and metabolites thereof. For example, the compounds of Formula I, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I may exist as clathrates or other complexes. Included within the scope of the invention are complexes such as clathrates, drug-host inclusion complexes wherein, in contrast to the aforementioned solvates, the drug and host are present in stoichiometric or non-stoichiometric amounts. Also included are complexes of Formula I containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of Formula I may have asymmetric carbon atoms. The carbon-carbon bonds of the compounds of Formula I may be depicted herein using a solid line (-), a solid wedge ( ━━ ), or a dotted wedge ( ⋯⋯ ).

The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of Formula I, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of Formula I may exhibit the phenomena of tautomerism and structural isomerism. For example, the compounds of Formula I may exist in several tautomeric forms, including the enol and imine forms, and the keto and enamine forms, and geometric isomers and mixtures thereof. All such tautomeric forms are included within the scope of compounds of Formula I. Tautomers exist as mixtures of a tautomeric set in solution. In solid form, usually one tautomer predominates. Even though one tautomer may be described, the present invention includes all tautomers of the compounds of Formula I.

The present invention also includes isotopically-labeled compounds, which are identical to those recited in Formula I above, but for the fact that one or more atoms are replaced by an atom having an atomic mass or mass number different from the atomic mass or mass number usually found in nature. Examples of isotopes that may be incorporated into compounds of Formula I include isotopes of hydrogen, carbon, nitrogen, oxygen, phosphorus, fluorine and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$. Certain isotopically-labeled compounds of Formula I, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically-labeled compounds of Formula I may generally be prepared by carrying out the procedures disclosed in the Schemes and/or in the Examples and Preparations below, by substituting an isotopically-labeled reagent for a non-isotopically-labeled reagent.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (i.e., decyl, lauryl, myristyl, and stearyl chlorides, bromides, and iodides), arylalkyl halides (i.e., benzyl and phenethyl bromides), and others.

In one embodiment, hemisalts of acids and bases may also be formed, for example, hemisulphate and hemicalcium salts.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts. The term "therapeutically effective amount" as used herein refers to that amount of the compound being administered which will relieve to some extent one or more of the symptoms of the disorder being treated.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The compounds of the invention may be administered orally. Oral administration may involve swallowing, so that the compound enters the gastrointestinal tract, or buccal or sublingual administration may be employed by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compounds of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (i.e., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions) may be formulated according to the known art using suitable dispersing, wetting, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, J. Pharm. Sci., 88 (10), 955-958 (1999).

Formulations suitable for topical administration to the eye include, for example, eye drops wherein the compound of this invention is dissolved or suspended in a suitable carrier. A typical formulation suitable for ocular or aural administration may be in the form of drops of a micronised suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

In another embodiment, the invention relates to the novel intermediates useful for preparing the compounds of the invention.

General Synthetic Schemes

The compounds of formula I may be prepared by the methods described below, together with synthetic methods known in the art of organic chemistry, or modifications and derivatizations that are familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-XII (published by Wiley-Interscience)). Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Experimental Procedures and Working Examples ambient temperature. The toluenesulfonylmethyl isocyanide [tosmic] reagent VII is prepared from aldehyde VI, 4-methylbenzenesulfinic acid, formamide and trimethylsilyl chloride, following the two-step general procedure described in the literature (*Organic Syntheses*; Wiley & Sons: New York, 2004; Collect. Vol. 10, p. 692). Imidazole II is then formed by reacting imine V and tosmic reagent VII with a carbonate base such as sodium carbonate or preferably potassium carbonate in a suitably polar, inert solvent such as dimethylacetamide, 1-methyl-2-pyrrolidinone or preferably N,N-dimethylformamide [DMF] at from 0° C. to 50° C., preferably at ambient temperature. The compound of Formula Ib is prepared from compound II by first removing the BOC protecting group under acidic conditions, using preferably trifluoroacetic acid [TFA] neat or as a solution in dichloromethane, or with HCl in alcoholic solvents, preferably methanol or ethanol. Reductive amination of the resulting secondary amine with aldehydes or ketones of formula $R^3R^4L{=}O$ yields the compound of Formula Ib. Where $R^3R^4L{=}O$ is an aldehyde, this transformation is preferably performed by mixing compound II and

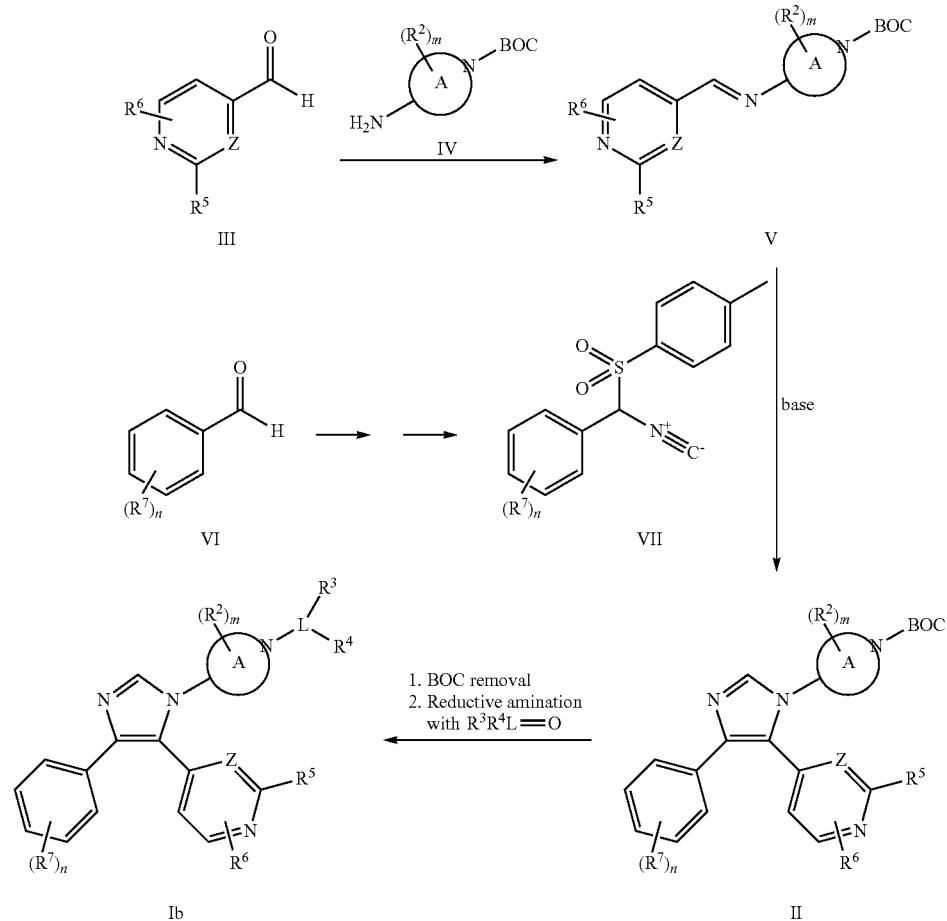

The compounds of Formula Ib, where $R^1$ is H, may be prepared as shown in Scheme I. The imine of Formula V is prepared by reaction of aldehyde III and an amino-substituted BOC-protected [BOC=tert-butoxycarbonyl]cyclic amine IV in a suitably inert solvent such as diethyl ether or preferably tert-butyl methyl ether at from 0° C. to 50° C., preferably at said aldehyde in dichloromethane, 1,2-dichloroethane or preferably tetrahydrofuran [THF] and then adding a suitable hydride reducing agent such as sodium cyanoborohydride or preferably sodium triacetoxyborohydride, with or without the presence of acetic acid as a co-solvent, at temperatures from 0° C. to 100° C., preferably at ambient temperature to 50° C.

This transformation may also be accomplished by formation of a discrete imino intermediate via the combination of the aldehyde R³R⁴L=O and compound II in the presence of a dehydrating reagent such as: titanium(IV) chloride or titanium(IV) isopropoxide in a non-reactive solvent such as THF or dichloromethane; magnesium sulfate in methanol or ethanol; or para-toluenesulfonic acid in refluxing toluene with azeotropic removal of water. Subsequent reduction of the resulting imino species with a hydride reagent such as sodium borohydride, sodium cyanoborohydride, or sodium triacetoxyborohydride, or by hydrogenation in the presence of a suitable metal catalyst such as palladium on carbon or palladium hydroxide, affords the compound of Formula Ib.

An alternative method to prepare pyrimidine compounds of Formula Ic is shown in Scheme II. The imine of Formula VIII is first prepared by reaction of 2-oxopropanal and amino-substituted BOC-protected cyclic amine IV, then reacted with tosmic reagent VII in similar fashion to that described for the formation of imidazole II in Scheme I, to yield the acetyl-substituted imidazole IX. Vinylogous amide X is prepared by heating IX with tert-butoxybis(dimethylamino)methane, or preferably N,N-dimethylformamide dimethyl acetal, either neat or in a suitably non-reactive solvent such as dichloromethane, at temperatures from ambient to 120° C. where 75-100° C. is preferred. Pyrimidines of Formula IIa where a hydrogen occupies the 2-position may be prepared from X by

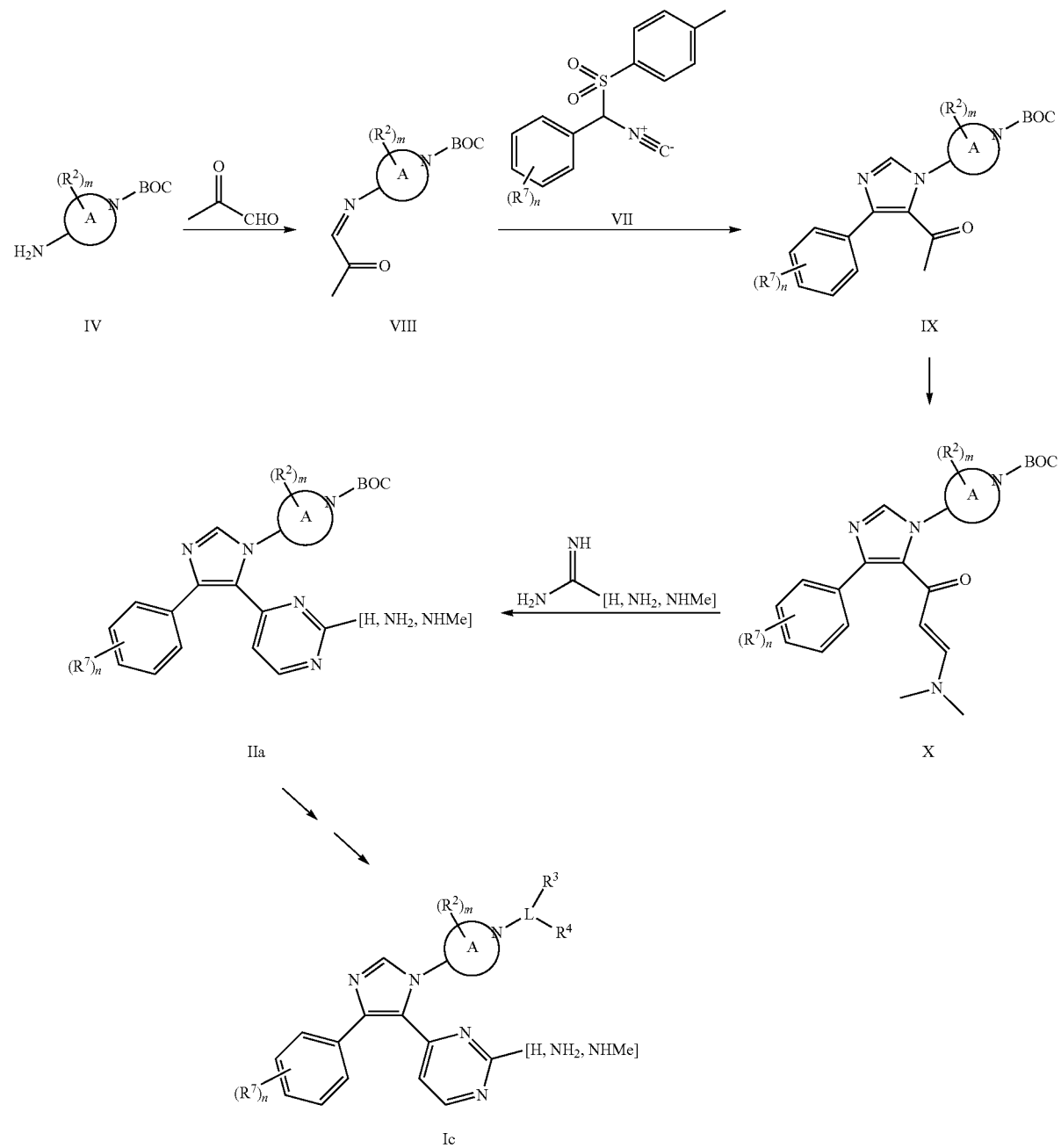

treatment with refluxing formamide or a formamide acetate melt at temperatures from 50° C. to 120° C. Likewise, treatment with a guanidine salt or a substituted guanidine salt in the presence of an alkoxide base such as sodium ethoxide or sodium methoxide in alcohol solvent such as ethanol or methanol, at 0° C. to reflux where ambient to 50° C. is preferred, yields 2-amino-substituted pyrimidine IIa. Preparation of compounds of Formula Ic is carried out from compound IIa using the same general methods described in Scheme I for the transformation of compound II to compound Ib.

Compounds wherein $R^1$ may be $C_{1-3}$alkyl or $C_{3-4}$cycloalkyl (Formula I) can be prepared according to the procedures shown in Scheme III. Following a modification of the procedure described in *Organic Syntheses*; Wiley & Sons: New York, 2004; Collect. Vol. 10, p. 692, aldehyde VI is treated with an amide and trimethylsilyl chloride in a mixture of acetonitrile and toluene at preferably elevated temperatures. 4-Methylbenzenesulfinic acid is added to provide arylsulfonylamide XI. Following the procedure described by J. A. Murry et al., *J. Am. Chem. Soc.* 2001, 123, 9696-9697, XI is typically treated with aldehyde III, a thiazolium catalyst and triethylamine, to yield amidoketone XII. Condensation with amino-substituted heterocycloalkyl compound IVa in the presence of acetic acid in an alcohol solvent such as methanol or ethanol provides the compound of Formula I.

Scheme III

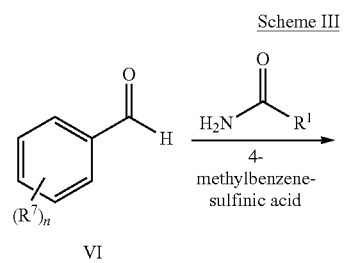

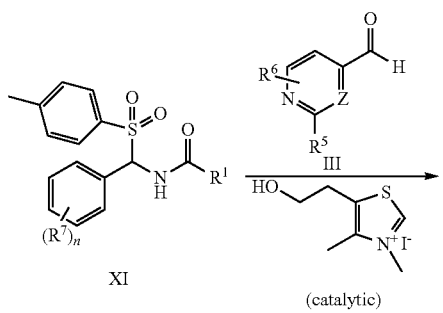

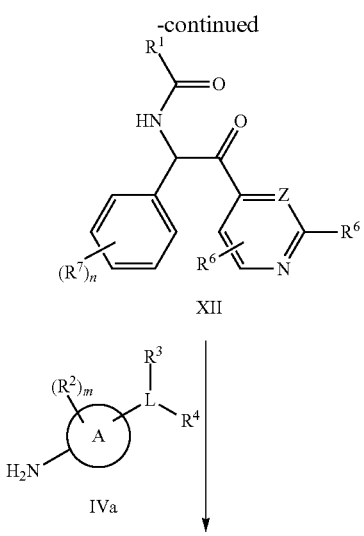

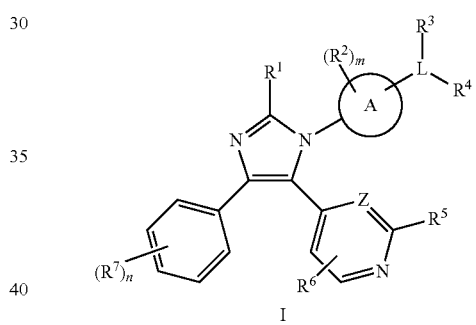

5,6,7,8-Tetrahydroimidazo[1,2-a]pyrazines of Formula XIX may be prepared following the synthetic sequence outlined in Scheme IV. Ketone XV may be prepared by condensing aryl ester XIII with the anion of methylheteroaryl compound XIV. This anion may be generated using suitable amide bases such as lithium diisopropylamide [LDA] or lithium hexamethyldisilazide [LHMDS] in non-reactive solvents such as THF or dialkyl ethers. Oxidation of XV to afford diketone XVI may be accomplished with HBr in DMSO. Imidazole acetal XVII is formed via condensation of XVI with dimethoxyacetaldehyde in the presence of ammonium acetate in an ethereal solvent such as diethyl ether or tert-butyl methyl ether. Treatment of XVII with aqueous acid, for instance HCl in THF/water, affords the unmasked aldehyde XVIII, which is mixed with an inert solvent such as THF, and treated in step-wise fashion in a single reaction with: 2-bromoethylamine in the presence of an acid scavenger such as triethylamine; a hydride reducing agent such as sodium triacetoxyborohydride; and BOC anhydride, to give regioisomeric compounds XIXa/b. XIXa may be further derivatized as shown in the previous Schemes to provide compounds of Formula I.

Scheme IV

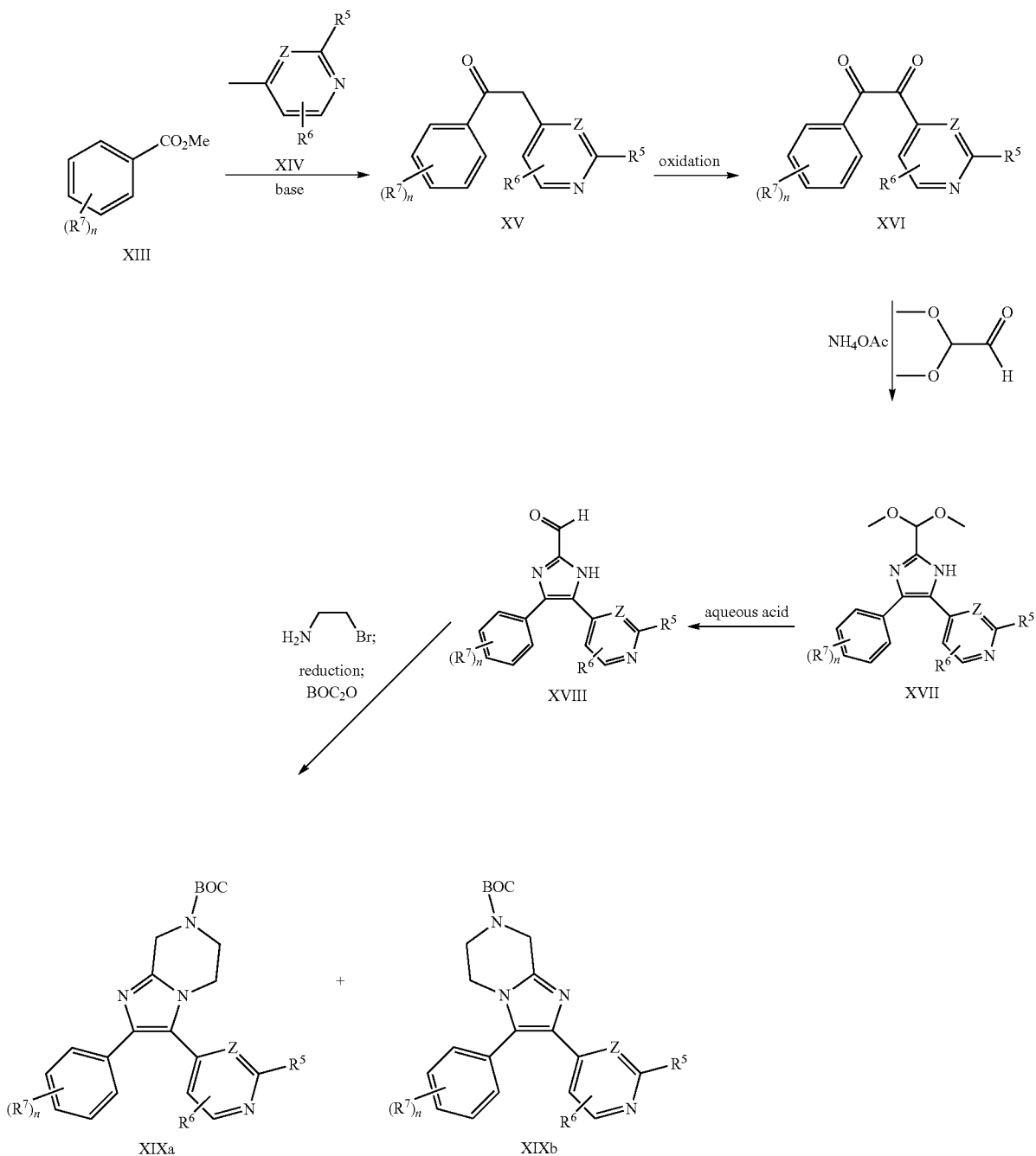

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.).

Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary

EXAMPLES

Example 1

4-{4-(4-Fluorophenyl)-1-[1-(pyrimidin-2-ylmethyl) azetidin-3-yl]-1H-imidazol-5-yl}pyrimidin-2-amine (1)

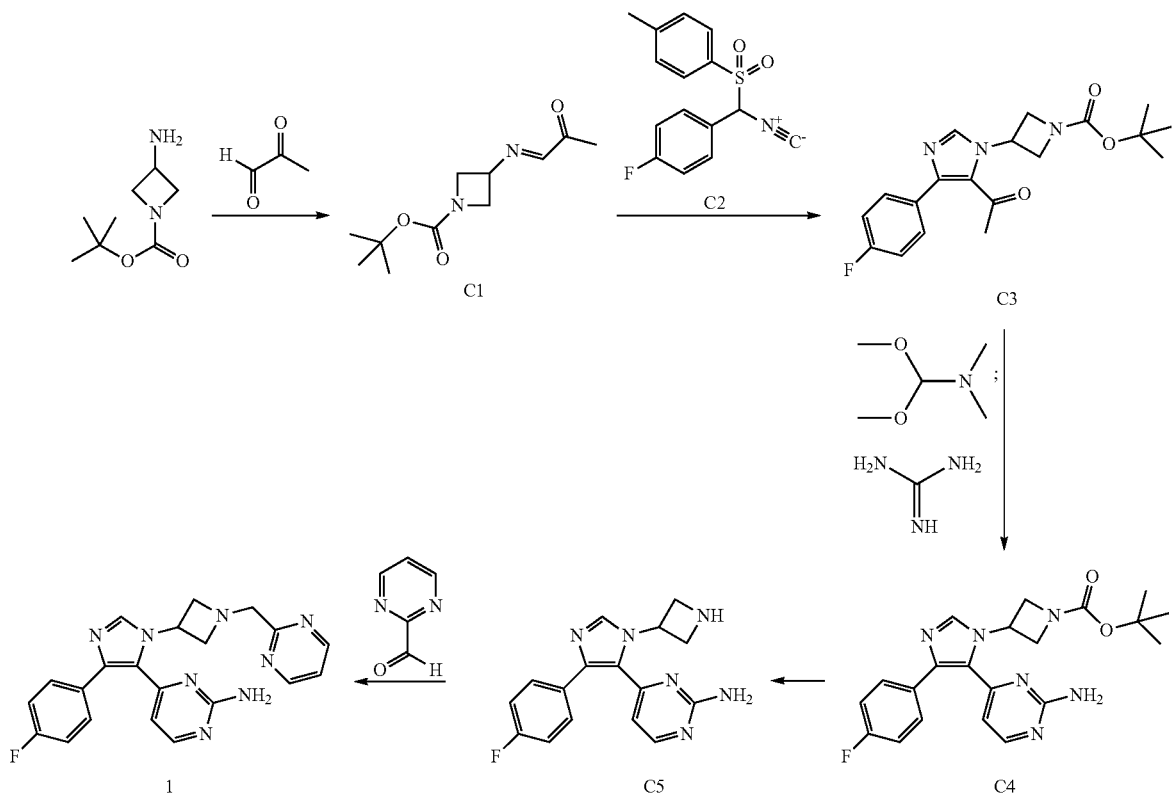

tert-Butyl 3-{[(1E)-2-oxopropylidene]amino}azetidine-1-carboxylate (C1)

A mixture of tert-butyl 3-aminoazetidine-1-carboxylate (16.8 g, 97.5 mmol) and 2-oxopropanal (10 g, 140 mmol) was stirred for 5 minutes at room temperature. The resulting material was purified via silica gel chromatography (Eluant: 1:1 petroleum ether: ethyl acetate) to give the product as an oil, which was used directly in the next step. Yield: 12.5 g, 55.2 mmol, 57%.

tert-Butyl 3-[5-acetyl-4-(4-fluorophenyl)-1H-imidazol-1-yl]azetidine-1-carboxylate (C3)

Potassium carbonate (15.0 g, 108 mmol) was added to a solution of 1-fluoro-4-{isocyano[(4-methylphenyl)sulfonyl]methyl}benzene (C2, see *Organic Syntheses*; Wiley & Sons: New York, 2004; Collect. Vol. 10, p. 692) (12.5 g, 43.2 mmol) and tert-butyl 3-{[(1E)-2-oxopropylidene]amino}azetidine-1-carboxylate (C1) (10 g, 44 mmol) in DMF (150 mL). The mixture was stirred for 16 hours at room temperature, then partitioned between ethyl acetate (500 mL) and water (500 mL). The organic layer was washed with water (3×500 mL), dried over sodium sulfate, filtered, and concentrated in vacuo. The residue was purified by silica gel chromatography (Eluant: 1:1 petroleum ether: ethyl acetate) to give the product as a solid. Yield: 11 g, 31 mmol, 72%.

tert-Butyl 3-[5-(2-aminopyrimidin-4-yl)-4-(4-fluorophenyl)-1H-imidazol-1-yl]azetidine-1-carboxylate (C4)

To a solution of tert-butyl 3-[5-acetyl-4-(4-fluorophenyl)-1H-imidazol-1-yl]azetidine-1-carboxylate (C3) (5.6 g, 15.6 mmol) in n-propanol (50 mL) was added N,N-dimethylformamide dimethyl acetal (12 g, 100 mmol), and the reaction mixture was stirred at 90° C. for 3 hours. At this point, guanidine hydrochloride (7.2 g, 75 mmol) and potassium carbonate (10 g, 72 mmol) were added to the reaction mixture. After stirring at 92° C. for an additional 16 hours, the reaction was treated with aqueous sodium hydroxide solution (5 N, 10 mL, 50 mmol), and stirring was continued for 16 hours at 92° C. After concentration in vacuo, the residue was partitioned between ethyl acetate (100 mL) and water (100 mL), and the aqueous phase was extracted with ethyl acetate (2×100 mL). The combined organic layers were dried over sodium sulfate, filtered, and concentrated under reduced pressure. The crude material was purified via silica gel chromatography (Eluant: 1:1 to 1:2 petroleum ether: ethyl acetate) to afford the product as a solid. Yield: 2.1 g, 5.1 mmol, 33%. NMR data was obtained from the product of a reaction run under similar conditions. $^1$H NMR (400 MHz, CD$_3$OD) δ 1.46 (s, 9H), 4.22 (dd, J=9, 5 Hz, 2H), 4.41 (dd, J=9, 9 Hz, 2H), 5.47 (m, 1H), 6.39 (d, J=5.1 Hz, 1H), 7.10 (dd, J=8.7, 8.7 Hz, 2H), 7.42-7.47 (m, 2H), 8.09 (d, J=5.3 Hz, 1H), 8.25 (s, 1H).

4-[1-Azetidin-3-yl-4-(4-fluorophenyl)-1H-imidazol-5-yl]pyrimidin-2-amine (C5)

To a solution of tert-butyl 3-[5-(2-aminopyrimidin-4-yl)-4-(4-fluorophenyl)-1H-imidazol-1-yl]azetidine-1-carboxylate (C4) (2.1 g, 5.1 mmol) in methanol (10 mL) was added aqueous hydrochloric acid (5 N, 30 mL) and the reaction was stirred for 2 hours at room temperature. The solution was concentrated and the residue was diluted with water (100 mL) and ethyl acetate (100 mL). After adjusting the mixture to pH=9 with aqueous ammonia, the aqueous layer was extracted with ethyl acetate (100 mL). The combined organic layers were dried over sodium sulfate, filtered, and concentrated in vacuo to give the product as a solid. Yield: 1.1 g, 3.5 mmol, 69%. LCMS m/z 311.4 (M+1). $^1$H NMR (400 MHz, CD$_3$OD) δ 3.95 (br d, J=7.5 Hz, 4H), 5.51 (m, 1H), 6.38 (br d, J=5.2 Hz, 1H), 7.10 (br dd, J=8.5, 8.5 Hz, 2H), 7.44 (br dd, J=8, 5 Hz, 2H), 8.10 (br d, J=5.0 Hz, 1H), 8.21 (br s, 1H).

4-{4-(4-Fluorophenyl)-1-[1-(pyrimidin-2-ylmethyl) azetidin-3-yl]-1H-imidazol-5-yl}pyrimidin-2-amine (1)

A mixture of 4-[1-azetidin-3-yl-4-(4-fluorophenyl)-1H-imidazol-5-yl]pyrimidin-2-amine (C5) (11.2 mg, 0.0361 mmol), pyrimidine-2-carbaldehyde (5.9 mg, 0.055 mmol), triethylamine (0.010 mL, 0.072 mmol) and acetic acid (0.010 mL, 0.17 mmol) in 1,2-dichloroethane (1.0 mL) was stirred for 30 minutes. Sodium triacetoxyborohydride (22.9 mg, 0.11 mmol) was added and stirring was continued for an additional 18 hours, at which time the reaction was quenched with dilute aqueous sodium hydroxide solution. Extraction of the aqueous layer with 1,2-dichloroethane was followed by combination of the organic layers and concentration in vacuo. Purification of the residue was effected by reversed-phase HPLC (Gradient: 5% to 60% acetonitrile in water) to provide the product as a yellow oil. Yield: 1 mg, 0.0025 mmol, 7%. LCMS m/z 403.6 (M+1). $^1$H NMR (400 MHz, CD$_3$OD) δ 3.66-3.70 (m, 2H), 3.96-4.00 (m, 2H), 4.02 (s, 2H), 5.34 (m, 1H), 6.38 (d, J=5.2 Hz, 1H), 7.10 (dd, J=8.8, 8.8 Hz, 2H), 7.38 (t, J=4.9 Hz, 1H), 7.44 (dd, J=8.9, 5.4 Hz, 2H), 8.09 (d, J=5.2 Hz, 1H), 8.24 (br s, 1H), 8.77 (d, J=5.0 Hz, 2H).

Example 2

4-{4-(4-Fluorophenyl)-1-[1-(1-isoxazol-3-ylethyl) piperidin-4-yl]-1H-imidazol-5-yl}-N-methylpyrimidin-2-amine (2)

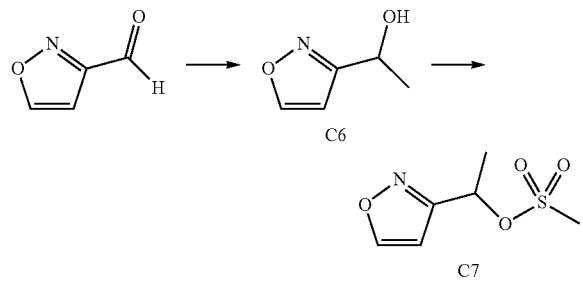

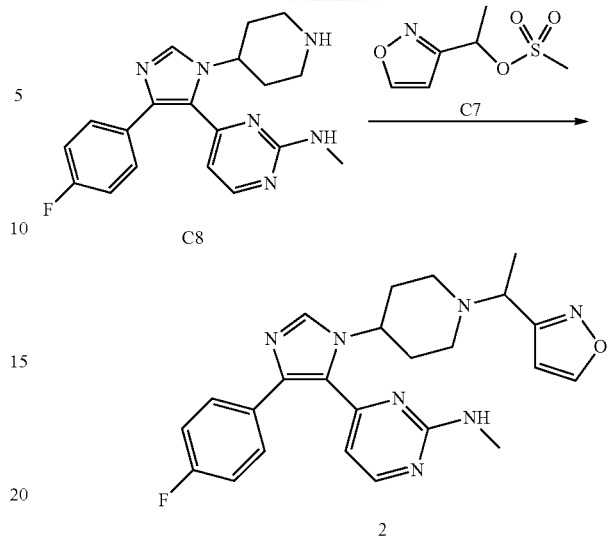

2

1-Isoxazol-3-ylethanol (C6)

A solution of isoxazole-3-carbaldehyde (1.00 g, 10.3 mmol) in THF (10 mL) was cooled to −78° C. and treated drop-wise with a solution of methylmagnesium iodide in diethyl ether (3.0 M, 3.50 mL, 10.5 mmol). The resulting solid layer was broken up with a spatula, and the reaction was allowed to warm to 0° C. over 1 hour. After an additional 1 hour of stirring at room temperature, the reaction was quenched with saturated aqueous ammonium chloride solution and extracted with ethyl acetate. The combined organic layers were washed with water and saturated aqueous sodium chloride solution, dried over magnesium sulfate, filtered, and concentrated in vacuo. Purification via silica gel chromatography (Eluant: 50% ethyl acetate in heptane) afforded the product as a yellow oil (536 mg, of 75-80% purity as judged by proton NMR spectroscopy), which was used directly in the next step. $^1$H NMR (400 MHz, CDCl$_3$), product peaks only: δ 1.58 (d, J=6.5 Hz, 3H), 2.34 (br d, J=4.4 Hz, 1H), 5.10 (qd, J=6.6, 4.7 Hz, 1H), 6.40 (d, J=1.7 Hz, 1H), 8.36 (d, J=1.7 Hz, 1H).

1-Isoxazol-3-ylethyl methanesulfonate (C7)

Methanesulfonic anhydride (825 mg, 4.74 mmol) was added to a solution of 1-isoxazol-3-ylethanol (C6 from the previous step, 536 mg) and triethylamine (0.90 mL, 6.5 mmol) in THF (10 mL), and the reaction mixture was stirred for 18 hours. After addition of ethyl acetate, the mixture was washed with water, dried over magnesium sulfate, filtered, and concentrated in vacuo. The reaction was judged to be incomplete by proton NMR spectroscopy, so this material was resubjected to the reaction conditions, using two equivalents of methanesulfonic anhydride, and worked up in the same manner. The crude material was purified by silica gel chromatography (Eluants: 25% ethyl acetate in heptane followed by 50% ethyl acetate in heptane) to provide the product as a colorless oil. Yield: 276 mg, 1.44 mmol, 14% over 2 steps. $^1$H NMR (400 MHz, CDCl$_3$) δ 1.81 (d, J=6.6 Hz, 3H), 3.01 (s, 3H), 5.93 (q, J=6.6 Hz, 1H), 6.50 (d, J=1.8 Hz, 1H), 8.45 (d, J=1.7 Hz, 1H).

4-{4-(4-Fluorophenyl)-1-[1-(1-isoxazol-3-ylethyl) piperidin-4-yl]-1H-imidazol-5-yl}-N-methylpyrimidin-2-amine (2)

A mixture of 4-[4-(4-fluorophenyl)-1-piperidin-4-yl-1H-imidazol-5-yl]-N-methylpyrimidin-2-amine (C8, which can be prepared by the method of J. Sisko, U.S. Pat. No. 6,239,279 B1, May 29, 2001) (75 mg, 0.21 mmol), 1-isoxazol-3-ylethyl methanesulfonate (C7) (60 mg, 0.31 mmol) and cesium carbonate (139 mg, 0.43 mmol) in acetonitrile (2 mL) was heated at 70° C. for 24 hours. Removal of solvent under reduced pressure provided a residue, which was purified by silica gel chromatography (Eluants: 0%, then 5%, then 15% methanol in ethyl acetate). The resulting colorless oil was dissolved in ethyl acetate/heptane, then concentrated in vacuo to provide the product as a white solid. Yield: 57 mg, 0.13 mmol, 62%. APCI m/z 448.3 (M+1). $^1$H NMR (400 MHz, CDCl$_3$) δ 1.46 (d, J=6.9 Hz, 3H), 1.93-2.07 (m, 2H), 2.12-2.24 (m, 4H), 2.98-3.08 (m, 2H), 3.02 (d, J=5.0 Hz, 3H), 3.94 (q, J=6.9 Hz, 1H), 4.59 (br m, 1H), 5.14 (br d, J=5 Hz, 1H), 6.35 (d, J=1.7 Hz, 1H), 6.40 (d, J=5.0 Hz, 1H), 7.00 (dd, J=8.8, 8.8 Hz, 2H), 7.46 (dd, J=9.0, 5.5 Hz, 2H), 7.77 (s, 1H), 8.15 (br d, J=5 Hz, 1H), 8.38 (dd, J=1.7, 0.6 Hz, 1H).

Example 3

4-{4-(4-Fluorophenyl)-1-[1-(pyrimidin-2-ylmethyl) piperidin-4-yl]-1H-imidazol-5-yl}pyrimidin-2-amine (3)

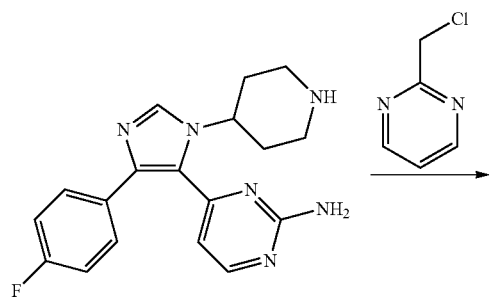

A slurry of 4-[4-(4-fluorophenyl)-1-piperidin-4-yl-1H-imidazol-5-yl]pyrimidin-2-amine, hydrochloride salt (C9, which can be prepared by the method of J. Sisko, U.S. Pat. No. 6,239,279 B1, May 29, 2001) (200 mg, 0.534 mmol), 2-(chloromethyl)pyrimidine (110 mg, 0.667 mmol) and cesium carbonate (365 mg, 1.12 mmol) in 2-methyltetrahydrofuran (3 mL) and water (1 mL) was heated overnight at 70° C. The resulting solution was cooled, and the organic layer was concentrated in vacuo. Addition of dichloromethane produced a solid; heptane (10 mL) was added, and the resulting mixture was stirred for 10 minutes. Filtration provided the title product as a solid. Yield: 205 mg, 0.476 mmol, 89%. APCI m/z 431.1 (M+1). $^1$H NMR (400 MHz, CD$_3$OD) δ 2.08-2.14 (m, 4H), 2.30-2.36 (m, 2H), 3.09 (br d, J=12 Hz, 2H), 3.84 (s, 2H), 4.62 (m, 1H), 6.40 (d, J=5.2 Hz, 1H), 7.07 (dd, J=8.8, 8.8 Hz, 2H), 7.39-7.43 (m, 3H), 8.04 (s, 1H), 8.13 (d, J=5.2 Hz, 1H), 8.80 (d, J=5.0 Hz, 2H).

Example 4

4-{4-(4-Fluorophenyl)-1-[1-(isoxazol-3-ylmethyl) piperidin-4-yl]-1H-imidazol-5-yl}pyrimidin-2-amine (4)

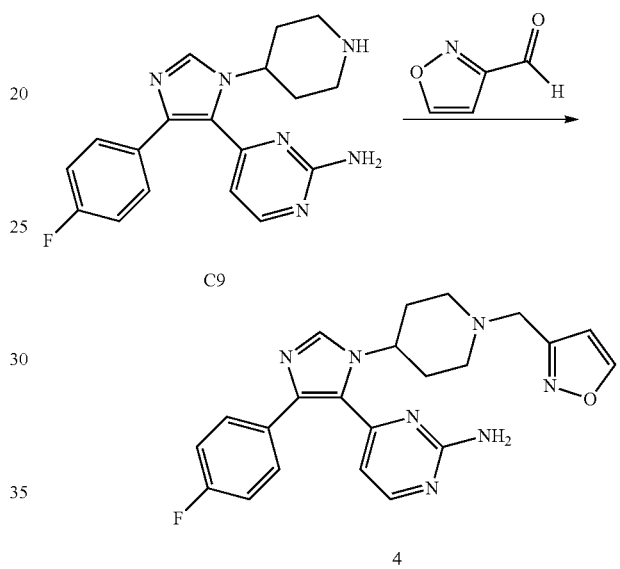

Isoxazole-3-carbaldehyde (3.5 g, 36 mmol) was added to a slurry of 4-[4-(4-fluorophenyl)-1-piperidin-4-yl-1H-imidazol-5-yl]pyrimidin-2-amine, hydrochloride salt (C9) (10.0 g, 26.7 mmol) in THF (20 mL) and dichloromethane (6 mL). After 30 minutes, sodium triacetoxyborohydride (95%, 17.9 g, 80.2 mmol) was added, and the reaction was allowed to stir for 18 hours. It was then quenched with saturated aqueous sodium bicarbonate solution (250 mL) and diluted with dichloromethane (400 mL). The aqueous layer was extracted with additional dichloromethane (250 mL), and the combined organic layers were dried over magnesium sulfate and filtered. At this point, the organic phase was combined with that of an identical reaction run on the same scale. Removal of solvents in vacuo provided a mixture of oil and solid, which was separated via pipette; the solid was slurried in diethyl ether (300 mL), filtered, and washed with fresh diethyl ether (150 mL), providing a white solid (16.7 g). The oil was mixed with diethyl ether (100 mL), and the resulting precipitate was collected by filtration to provide additional white solid (3.0 g). The combined crude product was subjected to chromatography on silica gel (Eluant: 25% methanol in ethyl acetate), and the purified material was precipitated from methanol solution to afford the title product as a white solid. Yield: 12.7 g, 30.3 mmol, 57%. APCI m/z 420.1 (M+1). $^1$H NMR (400 MHz, DMSO-d$_6$) δ 1.90-2.00 (m, 4H), 2.06-2.12 (m, 2H), 2.89 (br d, J=11.7 Hz, 2H), 3.61 (s, 2H), 4.25 (m, 1H), 6.41 (d, J=5.0 Hz, 1H), 6.53 (d, J=1.8 Hz, 1H), 6.80 (br s, 2H), 7.13

(dd, J=9.0, 9.0 Hz, 2H), 7.44 (dd, J=9.0, 5.6 Hz, 2H), 8.04 (s, 1H), 8.21 (d, J=5.0 Hz, 1H), 8.86 (d, J=1.7 Hz, 1H).

Example 5

4-{4-(4-Fluorophenyl)-1-[1-(isoxazol-3-ylmethyl) piperidin-4-yl]-1H-imidazol-5-yl}-N-methylpyrimidin-2-amine (5)

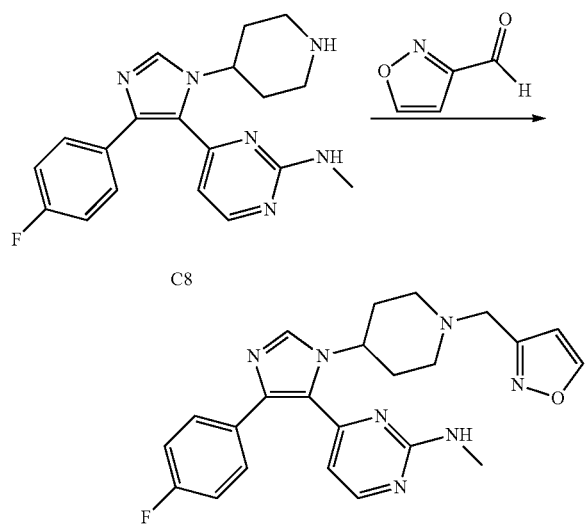

Sodium triacetoxyborohydride (135 mg, 0.637 mmol) was added to a solution of 4-[4-(4-fluorophenyl)-1-piperidin-4-yl-1H-imidazol-5-yl]-N-methylpyrimidin-2-amine (C8) (150 mg, 0.426 mmol) and isoxazole-3-carbaldehyde (49.6 mg, 0.511 mmol) in THF (10 mL). After 90 minutes at room temperature, the reaction was concentrated in vacuo and partitioned between saturated aqueous sodium bicarbonate solution and ethyl acetate. The aqueous layer was extracted with ethyl acetate, and the combined organic layers were washed with saturated aqueous sodium chloride solution, dried over magnesium sulfate, filtered, and concentrated under reduced pressure to provide a thick oil. Purification via silica gel chromatography (Eluants: ethyl acetate followed by 10% methanol in ethyl acetate) provided a viscous oil, which was reconcentrated from diethyl ether to afford the product as a white solid. Yield: 77 mg, 0.18 mmol, 42%. LCMS m/z 434.6 (M+1). $^1$H NMR (400 MHz, CDCl$_3$) δ 1.99-2.09 (m, 2H), 2.16-2.22 (m, 4H), 3.03 (m, 2H), 3.05 (d, J=5.1 Hz, 3H), 3.69 (s, 2H), 4.67 (br m, 1H), 5.17 (m, 1H), 6.41 (d, J=5.1 Hz, 1H), 6.41 (d, J=1.7 Hz, 1H), 7.00 (dd, J=8.7, 8.7 Hz, 2H), 7.46 (dd, J=8.7, 5.4 Hz, 2H), 7.77 (s, 1H), 8.16 (br d, J=4.5 Hz, 1H), 8.40 (d, J=1.6 Hz, 1H).

Example 6

4-{4-(4-Fluorophenyl)-1-[1-(isoxazol-3-ylmethyl) piperidin-4-yl]-1H-imidazol-5-yl}pyrimidine, hydrochloride salt (6)

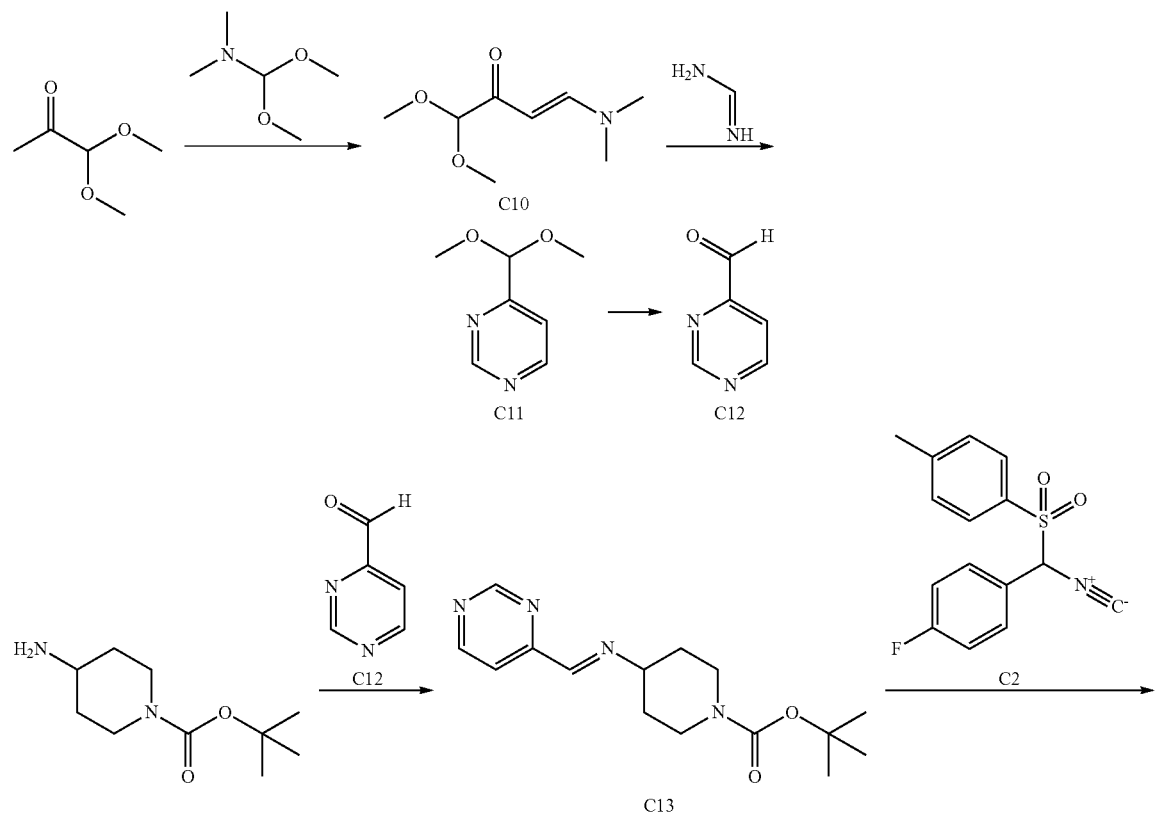

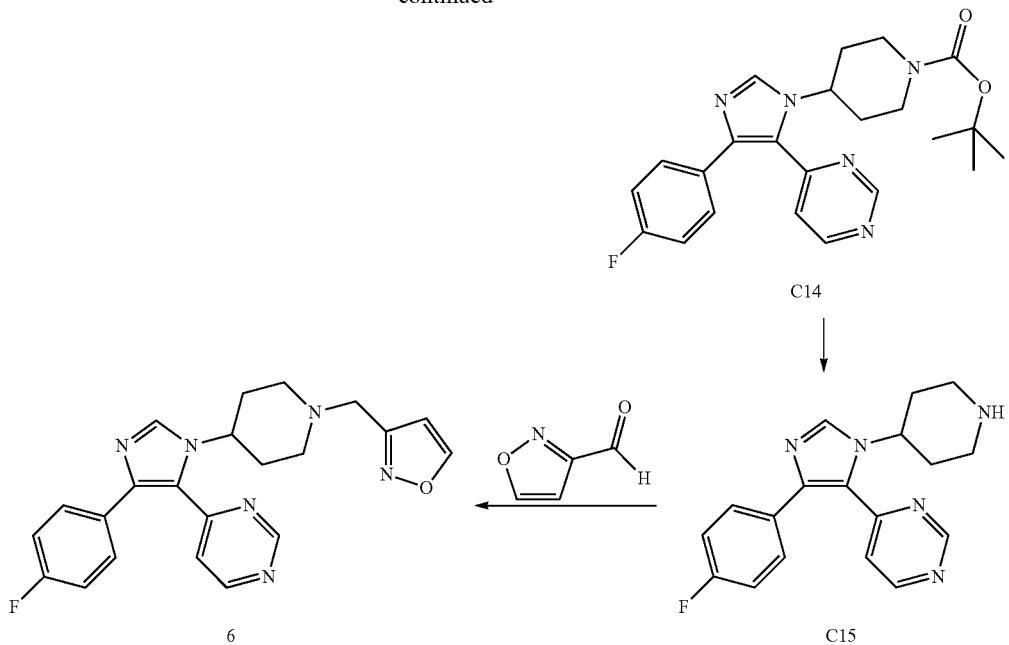

(3E)-4-(Dimethylamino)-1,1-dimethoxybut-3-en-2-one (C10)

A solution of N,N-dimethylformamide dimethyl acetal (147 g, 1.23 mol) and 1,1-dimethoxyacetone (146 g, 1.24 mol) in 2-butanol (1 L) was heated at reflux for 20 hours. After removal of solvent in vacuo, the residue was distilled under vacuum to provide the product as an oil. Yield: 145 g, 0.837 mol, 68%. Boiling point: 132-140° C./0.15 torr. NMR and MS data were obtained using the product of a reaction run under similar conditions. LCMS m/z 174.0 (M+1). $^1$H NMR (400 MHz, CDCl$_3$) δ 2.77 (br s, 3H), 3.02 (br s, 3H), 3.30 (s, 6H), 4.47 (s, 1H), 5.23 (br d, J=12.6 Hz, 1H), 7.63 (d, J=12.6 Hz, 1H).

4-(Dimethoxymethyl)pyrimidine (C11)

A mixture of (3E)-4-(dimethylamino)-1,1-dimethoxybut-3-en-2-one (C10) (147 g, 0.85 mol) and formamidine acetate (131 g, 1.26 mol) was heated at 110-120° C. for 4 hours. After cooling to room temperature, the reaction was poured into water (250 mL) and extracted with chloroform (5×100 mL). The combined organic layers were dried over sodium sulfate, filtered, and concentrated in vacuo. Distillation of the residue under vacuum afforded the product as an oil. Yield: 84 g, 0.54 mol, 64%. Boiling point: 45-50° C./0.2 torr. NMR data was obtained using the product of a reaction run under similar conditions. $^1$H NMR (400 MHz, CDCl$_3$) δ 3.30 (s, 6H), 5.21 (s, 1H), 7.46 (dd, J=5.1, 1.4 Hz, 1H), 8.68 (d, J=5.1 Hz, 1H), 9.12 (d, J=1.4 Hz, 1H).

Pyrimidine-4-carbaldehyde (C12)

A solution of 4-(dimethoxymethyl)pyrimidine (C11) (90 g, 0.58 mol) and concentrated hydrochloric acid (10 mL) in water (300 mL) was heated at 60-70° C. for 24 hours. The mixture was cooled and evaporated under reduced pressure to afford a glass-like mass, which was basified with aqueous potassium carbonate solution and extracted with ethyl acetate. The combined organic layers were concentrated in vacuo, and the residue was purified by distillation to afford the product as an oil. Yield: 16.3 g, 0.15 mol, 26%. GCMS m/z 108.0 (M$^+$). $^1$H NMR (400 MHz, DMSO-d$_6$) δ 7.90 (dd, J=5.0, 1.5 Hz, 1H), 9.14 (d, J=5.0 Hz, 1H), 9.49 (d, J=1.5 Hz, 1H), 9.96 (s, 1H).

tert-Butyl 4-{[(1E)-pyrimidin-4-ylmethylene]amino}piperidine-1-carboxylate (C13)

Pyrimidine-4-carbaldehyde (C12) (23.00 g, 212.8 mmol) was added to a mixture of tert-butyl 4-aminopiperidine-1-carboxylate (42.61 g, 212.8 mmol) in tert-butyl methyl ether (1.52 L). After 2.5 hours, the reaction was filtered, and the filtrate was concentrated in vacuo to provide an amber oil, which was generally taken directly to the following step. Yield: 56.30 g, 193.9 mmol, 91%. $^1$H NMR (400 MHz, CDCl$_3$) partial spectrum, characteristic peaks: δ 1.49 (s, 9H), 7.95 (dd, J=5.2, 1.5 Hz, 1H), 8.36 (s, 1H), 8.81 (d, J=5.2 Hz, 1H), 9.28 (d, J=1.5 Hz, 1H).

tert-Butyl 4-[4-(4-fluorophenyl)-5-pyrimidin-4-yl-1H-imidazol-1-yl]piperidine-1-carboxylate (C14)

A mixture of tert-butyl 4-{[(1E)-pyrimidin-4-ylmethylene]amino}piperidine-1-carboxylate (C13) (57.66 g, 198.6 mmol), 1-fluoro-4-{isocyano[(4-methylphenyl)sulfonyl]methyl}benzene (C2) (38.30 g, 132.4 mmol) and potassium carbonate (36.59 g, 264.8 mmol) in DMF (575 mL) was stirred for 18 hours. The reaction was filtered, and the solids were washed with ethyl acetate and discarded. The combined filtrates were diluted with ethyl acetate (1 L) and washed with water (2×1 L), and the combined aqueous layers were extracted with ethyl acetate (500 mL). Concentration of the combined organic layers in vacuo provided a solid, which was heated at reflux with tert-butyl methyl ether (400 mL), then cooled to room temperature and granulated for 1 hour. The solid was collected by filtration and washed with additional tert-butyl methyl ether; this filtrate was concentrated under reduced pressure and treated in the same way, using 75 mL of tert-butyl methyl ether, to obtain a second crop. The combined solids provided the product as a white solid. Yield: 41.70 g, 98.47 mmol, 74%. ¹H NMR (400 MHz, CDCl₃) δ 1.49 (s, 9H), 1.81-1.92 (m, 2H), 2.16 (br d, J=12 Hz, 2H), 2.77-2.85 (m, 2H), 4.30 (br s, 2H), 4.90 (tt, J=12.0, 3.8 Hz, 1H), 7.04 (dd, J=8.7, 8.7 Hz, 2H), 7.17 (dd, J=5.3, 1.4 Hz, 1H), 7.41 (dd, J=8.9, 5.4 Hz, 2H), 7.79 (s, 1H), 8.57 (d, J=5.4 Hz, 1H), 9.29 (d, J=1.5 Hz, 1H).

4-[4-(4-Fluorophenyl)-1-piperidin-4-yl-1H-imidazol-5-yl]pyrimidine (C15)

TFA (242 mL) was added to a solution of tert-butyl 4-[4-(4-fluorophenyl)-5-pyrimidin-4-yl-1H-imidazol-1-yl]piperidine-1-carboxylate (C14) (30.70 g, 72.49 mmol) in dichloromethane (242 mL). After 18 hours, the reaction was treated with aqueous sodium hydroxide solution (2 N) until the pH of the mixture reached 12.0. {Caution: potential exotherm!} The aqueous layer was extracted with dichloromethane (2×500 mL), and the combined organic layers were concentrated in vacuo to provide the product as a yellowish solid. Yield: 23.90 g, 73.91 mmol, quantitative. ¹H NMR (400 MHz, CDCl₃) δ 1.82-1.92 (m, 2H), 2.14 (br d, J=12 Hz, 2H), 2.71 (ddd, J=12.3, 12.3, 2.2 Hz, 2H), 3.22 (br d, J=12 Hz, 2H), 4.82 (tt, J=12.0, 3.9 Hz, 1H), 7.03 (dd, J=8.8, 8.8 Hz, 2H), 7.16 (dd, J=5.3, 1.4 Hz, 1H), 7.41 (dd, J=8.9, 5.4 Hz, 2H), 7.83 (s, 1H), 8.57 (d, J=5.3 Hz, 1H), 9.30 (d, J=1.4 Hz, 1H).

4-{4-(4-Fluorophenyl)-1-[1-(isoxazol-3-ylmethyl)piperidin-4-yl]-1H-imidazol-5-yl}pyrimidine, hydrochloride salt (6)

Sodium triacetoxyborohydride (29.99 g, 141.5 mmol) was added to a solution of 4-[4-(4-fluorophenyl)-1-piperidin-4-yl-1H-imidazol-5-yl]pyrimidine (C15) (30.50 g, 94.32 mmol) and isoxazole-3-carbaldehyde (10.99 g, 113.2 mmol) in THF (544 mL), and the reaction mixture was allowed to stir for 18 hours. The reaction was diluted with dichloromethane (330 mL) and treated with aqueous sodium bicarbonate solution (875 mL), which brought the pH to 9-10. The aqueous layer was extracted with dichloromethane (330 mL) and the combined organic layers were dried over magnesium sulfate, filtered and concentrated in vacuo. The resulting solid was purified by silica gel chromatography (Eluant: 5% methanol in dichloromethane), and the product was suspended in ethyl acetate (300 mL) and heated. Further addition of ethyl acetate (50 mL) provided a solution when heated at reflux; this was treated with a solution of HCl in diethyl ether (2 M, 89 mL, 178 mmol). After cooling to room temperature, the mixture was granulated for 30 minutes, at which time the solids were collected via filtration and washed with ethyl acetate. This material was then heated in ethanol (700 mL); methanol (150 mL) was added to generate a solution. The mixture was boiled down to a volume of 400 mL, and treated with additional ethanol (300 mL). After cooling to room temperature and granulating for 1 hour, the mixture was filtered and the solids were washed with ethanol, then heated to reflux in ethanol (247 mL). After cooling, the mixture was granulated for 1 hour, filtered and washed with ethanol to provide the product as a solid. The silica gel column was flushed with methanol and the eluant concentrated in vacuo to provide additional solid, which was dissolved in ethyl acetate (250 mL) by heating the mixture to reflux. Addition of a solution of HCl in diethyl ether (2 N, 30 mL, 60 mmol) was followed by cooling the mixture to room temperature and granulating it for 30 minutes. The hydrochloride salt was collected via filtration and washed with ethyl acetate; it was then heated to reflux in ethanol (114 mL), cooled, granulated for 1 hour, filtered and washed with ethanol to provide additional product as a solid. Combined yield of the two lots: 35.4 g, 80.3 mmol, 85%. LCMS data was obtained from the product of a reaction run under similar conditions. LCMS m/z 405.5 (M+1). ¹H NMR (400 MHz, CD₃OD) δ 2.53-2.69 (m, 4H), 3.36-3.45 (m, 2H), 3.81 (br d, J=12 Hz, 2H), 4.60 (br s, 2H), 5.17-5.25 (m, 1H), 6.86 (d, J=1.8 Hz, 1H), 7.28 (dd, J=8.7, 8.7 Hz, 2H), 7.37 (dd, J=5.3, 1.4 Hz, 1H), 7.50 (dd, J=8.9, 5.2 Hz, 2H), 8.80 (d, J=5.3 Hz, 1H), 8.87 (d, J=1.8 Hz, 1H), 9.42 (d, J=1.5 Hz, 1H), 9.58 (br s, 1H).

Example 7

4-{4-(4-Fluorophenyl)-[1-(isoxazol-3-ylmethyl)pyrrolidin-3-yl]-1H-imidazol-5-yl}pyrimidin-2-amine (7)

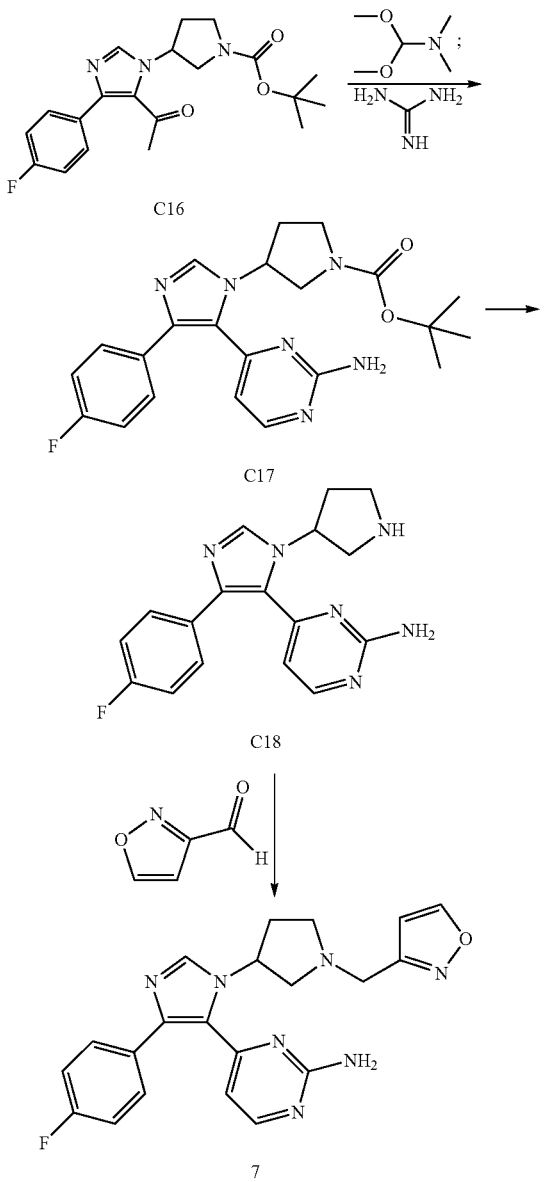

tert-Butyl 3-[5-(2-aminopyrimidin-4-yl)-4-(4-fluorophenyl)-1H-imidazol-1-yl]pyrrolidine-1-carboxylate (C17)

tert-Butyl 3-[5-acetyl-4-(4-fluorophenyl)-1H-imidazol-1-yl]pyrrolidine-1-carboxylate [C16, prepared according to the general procedure for the synthesis of tert-butyl 3-[5-acetyl-4-(4-fluorophenyl)-1H-imidazol-1-yl]azetidine-1-carboxylate (C3) in Example 1, except that tert-butyl 3-aminopyrrolidine-1-carboxylate was used in place of tert-butyl 3-aminoazetidine-1-carboxylate; NMR (400 MHz, CDCl$_3$) δ 1.49 (s, 9H), 2.13 (s, 3H), 2.22 (m, 1H), 2.45 (m, 1H), 3.47-3.88 (m, 4H), 5.55 (m, 1H), 7.15 (dd, J=8.7, 8.7 Hz, 2H), 7.46 (dd, J=8.7, 5.4 Hz, 2H), 7.69 (br s, 1H)] was subjected to reaction conditions similar to those used for preparation of tert-butyl 3-[5-(2-aminopyrimidin-4-yl)-4-(4-fluorophenyl)-1H-imidazol-1-yl]azetidine-1-carboxylate (C4) in Example 1, to provide the product as a solid. Yield: 6.1 g, 14.4 mmol, 67%. $^1$H NMR (400 MHz, CD$_3$OD) δ 1.48 (s, 9H), 2.32-2.50 (m, 2H), 3.48-3.65 (m, 3H), 3.81 (m, 1H), 5.42 (m, 1H), 6.42 (d, J=4.9 Hz, 1H), 7.09 (dd, J=8.7, 8.7 Hz, 2H), 7.43 (dd, J=8.5, 5.3 Hz, 2H), 7.92 (s, 1H), 8.13 (d, J=4.5 Hz, 1H).

4-[4-(4-Fluorophenyl)-1-pyrrolidin-3-yl-1H-imidazol-5-yl]pyrimidin-2-amine (C18)

tert-Butyl 3-[5-(2-aminopyrimidin-4-yl)-4-(4-fluorophenyl)-1H-imidazol-1-yl]pyrrolidine-1-carboxylate (C17) was converted to the product using the same conditions employed for transformation of tert-butyl 3-[5-(2-aminopyrimidin-4-yl)-4-(4-fluorophenyl)-1H-imidazol-1-yl]azetidine-1-carboxylate (C4) to 4-[1-azetidin-3-yl-4-(4-fluorophenyl)-1H-imidazol-5-yl]pyrimidin-2-amine (C5) in Example 1. The product was obtained as a solid. Yield: 3.3 g, 10 mmol, 69%. LCMS m/z 325.6 (M+1). $^1$H NMR (400 MHz, CD$_3$OD) δ 2.09-2.18 (m, 1H), 2.32-2.41 (m, 1H), 2.98-3.11 (m, 2H), 3.16-3.23 (m, 1H), 3.3 (m, 1H, assumed; obscured by solvent signal), 5.26 (m, 1H), 6.42 (d, J=5.1 Hz, 1H), 7.07 (dd, J=8.8, 8.8 Hz, 2H), 7.42 (dd, J=8.7, 5.4 Hz, 2H), 8.05 (s, 1H), 8.14 (d, J=5.3 Hz, 1H).

4-{4-(4-Fluorophenyl)-1-[1-(isoxazol-3-ylmethyl)pyrrolidin-3-yl]-1H-imidazol-5-yl}pyrimidin-2-amine (7)

To a solution of 4-[4(4-fluorophenyl)-1-pyrrolidin-3-yl-1H-imidazol-5-yl]pyrimidin-2-amine (C18) (300 mg, 0.925 mmol) and isoxazole-3-carbaldehyde (90 mg, 0.93 mmol) in toluene (5 mL) was added triethylamine (0.5 mL, 3.6 mmol), and the mixture was heated at 80° C. for 16 hours. After cooling to room temperature, the reaction was treated with sodium triacetoxyborohydride (500 mg, 2.36 mmol) and stirred for an additional 3 hours at 80° C. Solvents were removed in vacuo, and the residue was partitioned between ethyl acetate (20 mL) and water (20 mL). The aqueous layer was extracted with ethyl acetate (2×20 mL), and the combined organic layers were dried over sodium sulfate, filtered, and concentrated in vacuo. Purification by preparative thin layer chromatography on silica gel (Eluant: ethyl acetate) provided the product as a solid. Yield: 60 mg, 0.15 mmol, 16%. LCMS m/z 406.6 (M+1). $^1$H NMR (400 MHz, CD$_3$OD) δ 2.10 (m, 1H), 2.50-2.59 (m, 2H), 2.84 (dd, J=10.5, 6.7 Hz, 1H), 3.09 (dd, J=10.4, 2.4 Hz, 1H), 3.16 (m, 1H), 3.85 (AB quartet, J$_{AB}$=14.0 Hz, Δv$_{AB}$=23.1 Hz, 2H), 5.29 (m, 1H), 6.40 (d, J=4.9 Hz, 1H), 6.55 (br s, 1H), 7.07 (dd, J=8.7, 8.7 Hz, 2H), 7.41 (dd, J=8.5, 5.5 Hz, 2H), 8.12 (d, J=5.2 Hz, 1H), 8.21 (s, 1H), 8.63 (br s, 1H).

Example 8

4-{4-(4-Fluorophenyl)-1-[1-(isoxazol-3-ylmethyl)pyrrolidin-3-yl]-1H-imidazol-5-yl}pyrimidine (8)

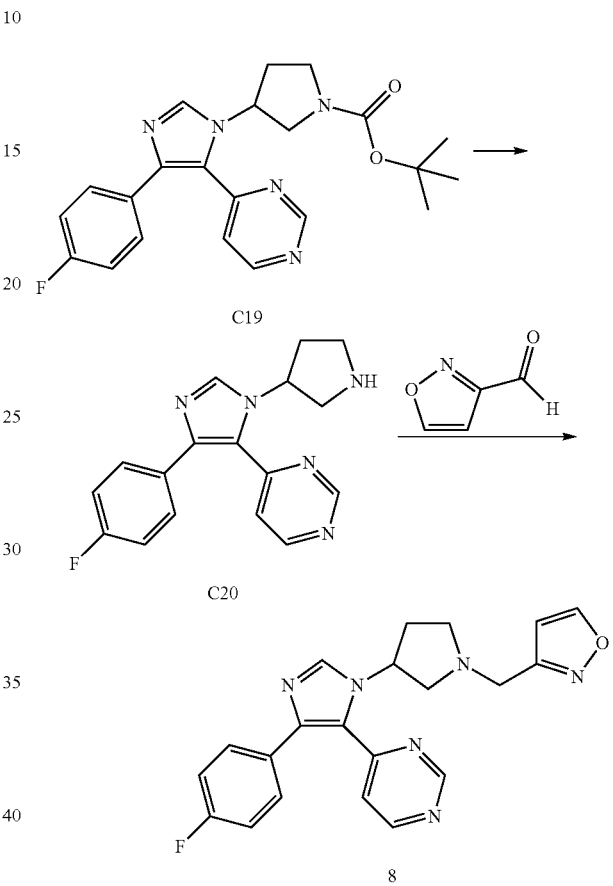

4-[4-(4-Fluorophenyl)-1-pyrrolidin-3-yl-1H-imidazol-5-yl]pyrimidine (C20)

tert-Butyl 3-[4-(4-fluorophenyl)-5-pyrimidin-4-yl-1H-imidazol-1-yl]pyrrolidine-1-carboxylate (C19, prepared according to the general procedure for the synthesis of tert-butyl 3-[5-(2-aminopyrimidin-4-yl)-4-(4-fluorophenyl)-1H-imidazol-1-yl]pyrrolidine-1-carboxylate (C17) in Example 7, except that formamidine acetate was used in place of guanidine hydrochloride) was converted to the product using conditions similar to those employed for transformation of tert-butyl 3-[5-(2-aminopyrimidin-4-yl)-4-(4-fluorophenyl)-1H-imidazol-1-yl]pyrrolidine-1-carboxylate (C17) to 4-[4-(4-fluorophenyl)-1-pyrrolidin-3-yl-1H-imidazol-5-yl]pyrimidin-2-amine (C18) in Example 7. The product was obtained as a solid. Yield: 1.58 g, 5.11 mmol, 70%. LCMS m/z 310.4 (M+1). $^1$H NMR (400 MHz, CD$_3$OD) δ 2.16 (m, 1H), 2.37 (m, 1H), 3.02 (m, 1H), 3.09 (dd, J=12.2, 4.6 Hz, 1H), 3.21 (m, 1H), 3.3 (m, 1H, assumed; obscured by solvent signal), 5.32 (m, 1H), 7.09 (dd, J=8.6, 8.6 Hz, 2H), 7.26 (d, J=5.2 Hz, 1H), 7.38 (dd, J=8.3, 5.5 Hz, 2H), 8.15 (s, 1H), 8.63 (d, J=5.5 Hz, 1H), 9.28 (s, 1H).

4-{4-(4-Fluorophenyl)-1-[1-(isoxazol-3-ylmethyl)pyrrolidin-3-yl]-1H-imidazol-5-yl}pyrimidine (8)

4-[4-(4-Fluorophenyl)-1-pyrrolidin-3-yl-1H-imidazol-5-yl]pyrimidine (C20) was converted to the product according to the general procedure for the synthesis of 4-{4-(4-fluorophenyl)-1-[1-(pyrimidin-2-ylmethyl)azetidin-3-yl]-1H-imidazol-5-yl}pyrimidin-2-amine (1) in Example 1, except that the crude product was purified by silica gel chromatography (Gradient: 50% to 100% ethyl acetate in heptane, followed by elution with 1% triethylamine in ethyl acetate). The product was obtained as a white solid. Yield: 205 mg, 0.525 mmol, 41%. LCMS m/z 391.0 (M+1). $^1$H NMR (400 MHz, CD$_3$OD) δ 2.07-2.16 (m, 1H), 2.48-2.58 (m, 2H), 2.82 (dd, J=10.5, 6.7 Hz, 1H), 3.12 (dd, J=10.5, 2.4 Hz, 1H), 3.15-3.20 (m, 1H), 3.85 (AB quartet, J$_{AB}$=13.9 Hz, Δv$_{AB}$=22.0 Hz, 2H), 5.30-5.35 (m, 1H), 6.54 (d, J=1.7 Hz, 1H), 7.09 (dd, J=8.9, 8.9 Hz, 2H), 7.24 (dd, J=5.4, 1.5 Hz, 1H), 7.38 (dd, J=8.9, 5.4 Hz, 2H), 8.29 (s, 1H), 8.61 (d, J=5.4 Hz, 1H), 8.63 (d, J=1.7 Hz, 1H), 9.26 (d, J=1.2 Hz, 1H).

Example 9

4-[4-(4-Fluorophenyl)-1-{1-[(1R)-1-isoxazol-3-ylethyl]piperidin-4-yl}-1H-imidazol-5-yl]pyrimidine (9)

Example 10

4-[4-(4-Fluorophenyl)-1-{1-[(1S)-1-isoxazol-3-ylethyl]piperidin-4-yl}-1H-imidazol-5-yl]pyrimidine (10)

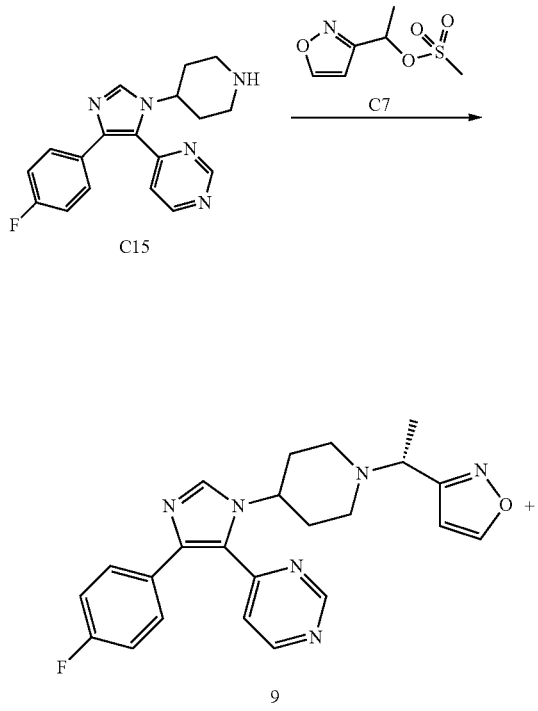

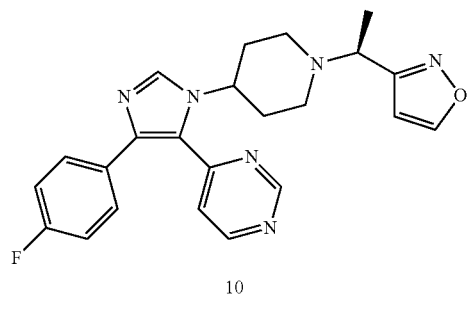

To a solution of 1-isoxazol-3-ylethyl methanesulfonate (C7) (1.2 g, 6.3 mmol) in DMF (40 mL) was added cesium carbonate (1.5 g, 4.6 mmol) and 4-[4-(4-fluorophenyl)-1-piperidin-4-yl-1H-imidazol-5-yl]pyrimidine (C15) (600 mg, 1.86 mmol), and the reaction was stirred at 60° C. for 18 hours. Ethyl acetate (200 mL) was added, and the mixture was washed with water (3×40 mL), washed with saturated aqueous sodium chloride solution, dried over sodium sulfate, filtered, and concentrated in vacuo. Purification of the residue by preparative HPLC (Column: Phenomenex Luna, 250×50 mm; Mobile phase A: 0.1% TFA in water; Mobile phase B: 0.1% TFA in acetonitrile; Gradient: 11% to 36% B) provided a mixture of the two enantiomeric products, which were separated by chiral HPLC (Column: Chiralcel OD, 250×20 mm, 10 μm; Mobile phase A: supercritical carbon dioxide; Mobile phase B: 2-propanol containing 0.05% diethylamine; Eluant: 60:40 A: B at 70 mL/minute) to provide 4-[4-(4-fluorophenyl)-1-{1-[(1R)-1-isoxazol-3-ylethyl]piperidin-4-yl}-1H-imidazol-5-yl]pyrimidine (9; absolute configuration is tentatively assigned) as a yellow oil (Yield: 30 mg, 0.072 mmol, 4%) [LCMS m/z 419.2 (M+1); $^1$H NMR (400 MHz, CDCl$_3$) δ 1.47 (d, J=6.9 Hz, 3H), 1.93-2.06 (m, 2H), 2.12-2.28 (m, 4H), 2.98-3.05 (m, 2H), 3.96 (q, J=6.9 Hz, 1H), 4.60-4.68 (m, 1H), 6.34 (d, J=1.4 Hz, 1H), 7.02 (dd, J=8.7, 8.7 Hz, 2H), 7.15 (dd, J=5.3, 1.3 Hz, 1H), 7.40 (dd, J=8.8, 5.5 Hz, 2H), 7.83 (s, 1H), 8.38 (br s, 1H), 8.55 (d, J=5.3 Hz, 1H), 9.27 (br s, 1H); Retention time 2.81 minutes using a Chiralpak OD-H column (250×4.6 mm, 5 μm; Mobile phase A: supercritical carbon dioxide; Mobile phase B: 2-propanol containing 0.05% diethylamine; Gradient: 5% to 40% B)] and 4-[4-(4-fluorophenyl)-1-{1-[(1S)-1-isoxazol-3-ylethyl]piperidin-4-yl}-1H-imidazol-5-yl]pyrimidine (113; absolute configuration is tentatively assigned) as a yellow oil (Yield: 30 mg, 0.072 mmol, 4%) [LCMS m/z 419.1 (M+1); $^1$H NMR (400 MHz, CDCl$_3$) δ 1.47 (d, J=6.9 Hz, 3H), 1.93-2.06 (m, 2H), 2.11-2.27 (m, 4H), 2.98-3.06 (m, 2H), 3.96 (q, J=6.9 Hz, 1H), 4.60-4.68 (m, 1H), 6.34 (d, J=1.5 Hz, 1H), 7.02 (dd, J=8.7, 8.7 Hz, 2H), 7.14 (br d, J=5.4 Hz, 1H), 7.39 (dd, J=8.7, 5.5 Hz, 2H), 7.83 (s, 1H), 8.39 (br s, 1H), 8.55 (d, J=5.3 Hz, 1H), 9.27 (br s, 1H); Retention time: 2.65 minutes, using a system identical to the analytical HPLC detailed above for the 1R enantiomer].

Example 11

2-{[4-(4-Phenyl-5-pyrimidin-4-yl-1H-imidazol-1-yl)piperidin-1-yl]methyl}pyrimidine (11)

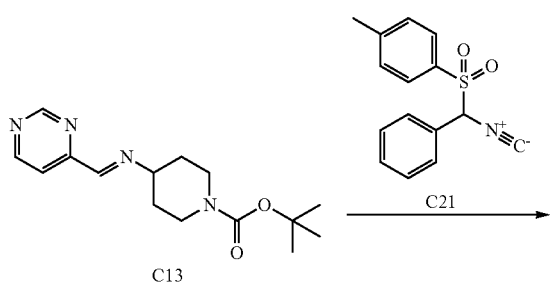

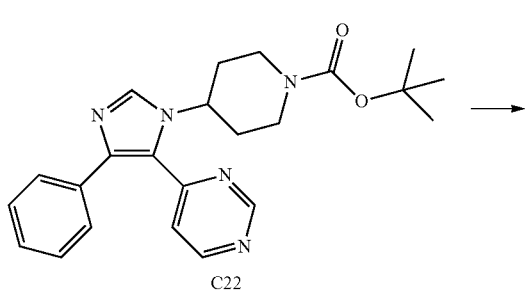

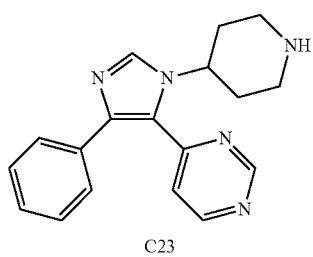

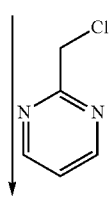

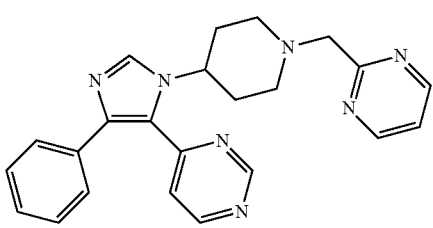

11 tert-Butyl 4-(4-phenyl-5-pyrimidin-4-yl-1H-imidazol-1-yl)piperidine-1-carboxylate (C22)

A mixture of potassium carbonate (107 mg, 0.774 mmol), 1-{[isocyano(phenyl)methyl]sulfonyl}-4-methylbenzene (C21, see *Organic Syntheses*; Wiley & Sons: New York, 2004; Collect. Vol. 10, p. 692) (0.209 g, 0.770 mmol) and tert-butyl 4-{[(1E)-pyrimidin-4-ylmethylene]amino}piperidine-1-carboxylate (C13) (582 mg, 2.00 mmol) in DMF (3 mL) was stirred for 18 hours at room temperature, then diluted with aqueous sodium hydroxide solution (1 N, 50 mL). The mixture was extracted with ethyl acetate, and the combined organic layers were washed with aqueous lithium chloride solution, dried over magnesium sulfate, filtered, and concentrated in vacuo. Purification via silica gel chromatography (Eluants: 50%, then 75% ethyl acetate in heptane) provided the product as a cream-colored solid. Yield: 267 mg, 0.658 mmol, 85%. APCI m/z 406.0 (M+1). $^1$H NMR (400 MHz, CDCl$_3$) δ 1.49 (s, 9H), 1.82-1.92 (m, 2H), 2.17 (br d, J=12 Hz, 2H), 2.77-2.86 (m, 2H), 4.26-4.34 (m, 2H), 4.93 (tt, J=12, 4 Hz, 1H), 7.20 (dd, J=5.3, 1.5 Hz, 1H), 7.32-7.36 (m, 3H), 7.42-7.45 (m, 2H), 7.80 (s, 1H), 8.54 (d, J=5.3 Hz, 1H), 9.28 (d, J=1.3 Hz, 1H).

4-(4-Phenyl-1-piperidin-4-yl-1H-imidazol-5-yl)pyrimidine (C23)

TFA (2 mL) was added to a solution of tert-butyl 4-(4-phenyl-5-pyrimidin-4-yl-1H-imidazol-1-yl)piperidine-1-carboxylate (C22) (267 mg, 0.658 mmol) in dichloromethane (5 mL). After 2 hours, the reaction was concentrated in vacuo, and then treated with saturated aqueous sodium bicarbonate solution. The mixture was extracted with warm ethyl acetate, and the combined organic layers were washed with saturated aqueous sodium chloride solution, dried over magnesium sulfate, filtered, and concentrated under reduced pressure. The resulting light yellow oil solidified over the course of several days to provide 105 mg of product that was contaminated with approximately 20% of a related impurity. Fine white needles precipitated out of the aqueous layer; these were collected by filtration to provide additional product as a cream colored solid. Yield from aqueous layer: 54 mg, 0.18 mmol, 27%. $^1$H NMR (400 MHz, CDCl$_3$) δ 1.83-1.93 (m, 2H), 2.12-2.18 (m, 2H), 2.72 (ddd, J=12.3, 12.3, 2.3 Hz, 2H), 3.20-3.25 (m, 2H), 4.85 (tt, J=12.0, 4.0 Hz, 1H), 7.19 (dd, J=5.3, 1.5 Hz, 1H), 7.30-7.36 (m, 3H), 7.42-7.45 (m, 2H), 7.85 (s, 1H), 8.54 (d, J=5.4 Hz, 1H), 9.30 (d, J=1.4 Hz, 1H).

2-{[4-(4-Phenyl-5-pyrimidin-4-yl-1H-imidazol-1-yl)piperidin-1-yl]methyl}pyrimidine (11)

The title product was prepared by reaction of 4-(4-phenyl-1-piperidin-4-yl-1H-imidazol-5-yl)pyrimidine (C23) with 2-(chloromethyl)pyrimidine according to the general procedure for the synthesis of 4-{4-(4-fluorophenyl)-1-[1-(pyrimidin-2-ylmethyl)piperidin-4-yl]-1H-imidazol-5-yl}pyrimidin-2-amine (3) in Example 3. In this case, after the reaction mixture was concentrated, the residue was partitioned between ethyl acetate and water. The organic layer was washed with saturated aqueous sodium chloride solution, dried over magnesium sulfate, filtered and concentrated under reduced pressure. Purification was effected via silica gel chromatography (Eluant: 25% methanol in ethyl acetate) to provide the product as a white solid. Yield: 63 mg, 0.16 mmol, 62%. APCI m/z 398.1 (M+1). $^1$H NMR (400 MHz, CDCl$_3$) δ 2.11-2.20 (m, 4H), 2.23-2.32 (m, 2H), 3.13 (br d, J=12 Hz, 2H), 3.87 (s, 2H), 4.78 (tt, J=11, 4.5 Hz, 1H), 7.18 (dd, J=5.3, 1.5 Hz, 1H), 7.22 (t, J=4.9 Hz, 1H), 7.29-7.34 (m, 3H), 7.41-7.44 (m, 2H), 7.85 (s, 1H), 8.53 (br d, J=5.4 Hz, 1H), 8.76 (d, J=4.9 Hz, 2H), 9.29 (br d, J=1.5 Hz, 1H).

Example 12

N-Methyl-4-{4-phenyl-1-[1-(pyrimidin-2-ylmethyl)piperidin-4-yl]-1H-imidazol-5-yl}pyrimidin-2-amine (12)

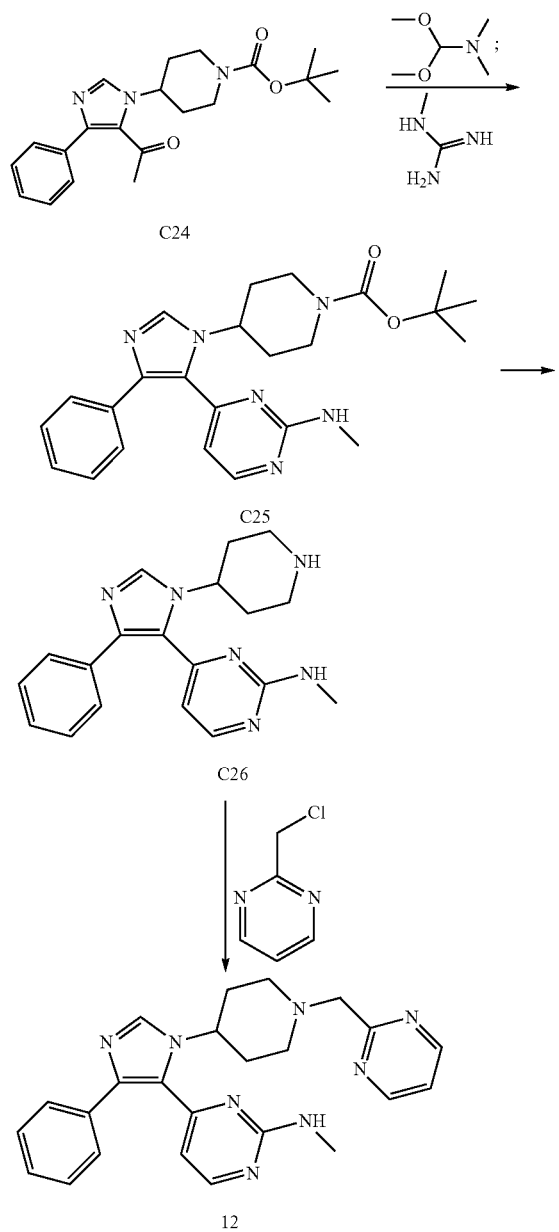

tert-Butyl 4-{5-[2-(methylamino)pyrimidin-4-yl]-4-phenyl-1H-imidazol-1-yl}piperidine-1-carboxylate (C25)

A mixture of tert-butyl 4-(5-acetyl-4-phenyl-1H-imidazol-1-yl)piperidine-1-carboxylate [C24, prepared according to the general procedure for the synthesis of tert-butyl 3-[5-acetyl-4-(4-fluorophenyl)-1H-imidazol-1-yl]azetidine-1-carboxylate (C3) in Example 1, except that tert-butyl 4-aminopiperidine-1-carboxylate was used in place of tert-butyl 3-aminoazetidine-1-carboxylate, and 1-{[isocyano(phenyl)methyl]sulfonyl}-4-methylbenzene (C21) was employed rather than 1-fluoro-4-{isocyano[(4-methylphenyl)sulfonyl]methyl}benzene (C2)] (414 mg, 1.12 mmol) and N,N-dimethylformamide dimethyl acetal (4 mL) was heated to 100° C. for 18 hours, then cooled and concentrated in vacuo. The residue was dissolved in anhydrous methanol (2 ml) and added to a solution of N-methylguanidine in methanol [prepared by reacting sodium metal (70 mg, 3 mmol) with anhydrous methanol (2 mL), then adding N-methylguanidine hydrochloride (413 mg, 3.77 mmol) to the resulting sodium methoxide solution]. The reaction mixture was heated at 50° C. for 21 hours, then cooled to room temperature and treated with water (1 mL). The solids were collected by filtration, rinsed with saturated aqueous sodium bicarbonate solution and water and dried to provide the product as a light tan solid. Yield: 230 mg, 0.53 mmol, 47%. APCI m/z 435.0 (M+1). $^1$H NMR (400 MHz, CDCl$_3$) δ 1.49 (s, 9H), 1.82-1.93 (m, 2H), 2.19 (br d, J=12 Hz, 2H), 2.73-2.82 (m, 2H), 3.06 (d, J=5.1 Hz, 3H), 4.26-4.35 (m, 2H), 4.81-4.90 (m, 1H), 5.16-5.21 (m, 1H), 6.45 (d, J=5.1 Hz, 1H), 7.28-7.34 (m, 3H), 7.48-7.51 (m, 2H), 7.75 (s, 1H), 8.15 (br d, J=4.9 Hz, 1H).

N-Methyl-4-(4-phenyl-1-piperidin-4-yl-1H-imidazol-5-yl)pyrimidin-2-amine (C26)

The title compound was prepared from tert-butyl 4-{5-[2-(methylamino)pyrimidin-4-yl]-4-phenyl-1H-imidazol-1-yl}piperidine-1-carboxylate (C25) according to the general procedure for the synthesis of 4-(4-phenyl-1-piperidin-4-yl-1H-imidazol-5-yl)pyrimidine (C23) in Example 11. In this case, after the organic layers were dried over magnesium sulfate, filtered, and concentrated under reduced pressure, the product was obtained as a white solid. Yield: 174 mg, 0.520 mmol, 100%. APCI m/z 335.0 (M+1). $^1$H NMR (400 MHz, CD$_3$OD) δ 2.09-2.20 (m, 2H), 2.37 (br d, J=12 Hz, 2H), 2.97 (s, 3H), 3.0-3.04 (m, 2H), 3.41-3.46 (m, 2H), 4.93 (tt, J=12, 4 Hz, 1H, assumed; partially obscured by water signal), 6.33 (d, J=5.1 Hz, 1H), 7.27-7.35 (m, 3H), 7.37-7.41 (m, 2H), 8.05 (s, 1H), 8.09 (d, J=5.1 Hz, 1H).

N-Methyl-4-{4-phenyl-1-[1-(pyrimidin-2-ylmethyl)piperidin-4-yl]-1H-imidazol-5-yl}pyrimidin-2-amine (12)

The title product was prepared by reaction of N-methyl-4-(4-phenyl-1-piperidin-4-yl-1H-imidazol-5-yl)pyrimidin-2-amine (C26) with 2-(chloromethyl)-pyrimidine according to the general procedure for the synthesis of 4-{4-(4-fluorophenyl)-1-[1-(pyrimidin-2-ylmethyl)piperidin-4-yl]-1H-imidazol-5-yl}pyrimidin-2-amine (3) in Example 3. In this case, after the reaction cooled to room temperature, it was diluted with dichloromethane (20 mL) and water (2 mL). The organic layer was dried over magnesium sulfate, filtered and concentrated in vacuo to provide a light yellow solid, which was dissolved in a small volume of dichloromethane. Addition of heptane caused a solid to precipitate; this mixture was stirred for 30 minutes and then the solid was collected by filtration, washed with heptane and washed with diethyl ether to provide the product as a light yellow solid. Yield: 106 mg, 0.248 mmol, 34%. APCI m/z 427.1 (M+1). $^1$H NMR (400 MHz, CD$_3$OD) δ 2.12-2.17 (m, 4H), 2.29-2.36 (m, 2H), 2.97 (s, 3H), 3.11 (br d, J=12 Hz, 2H), 3.85 (s, 2H), 4.74 (br s, 1H), 6.34 (d, J=5.1 Hz, 1H), 7.29-7.35 (m, 3H), 7.38-7.43 (m, 3H), 8.06 (s, 1H), 8.09 (br d, J=5 Hz, 1H), 8.80 (d, J=4.9 Hz, 2H).

Example 13

4-{1-[1-(Isoxazol-3-ylmethyl)piperidin-4-yl]-4-phenyl-1H-imidazol-5-yl}pyrimidin-2-amine, hydrochloride salt (13)

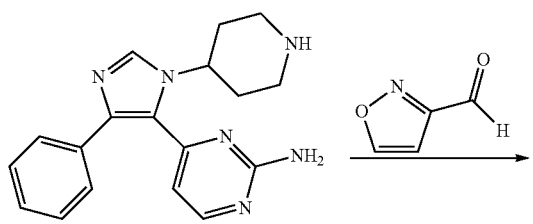

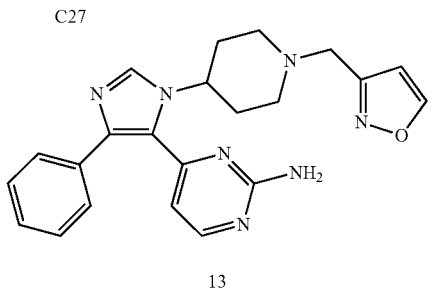

4-(4-Phenyl-1-piperidin-4-yl-1H-imidazol-5-yl)pyrimidin-2-amine [C27, prepared from tert-butyl 4-(5-acetyl-4-phenyl-1H-imidazol-1-yl)piperidine-1-carboxylate (C24) in a manner similar to the synthesis of N-methyl-4-(4-phenyl-1-piperidin-4-yl-1H-imidazol-5-yl)pyrimidin-2-amine (C26) described in Example 12, but using guanidine hydrochloride in place of N-methylguanidine hydrochloride] was reacted with isoxazole-3-carbaldehyde according to the general procedure for the synthesis of 4-{4-(4-fluorophenyl)-1-[1-(isoxazol-3-ylmethyl)piperidin-4-yl]-1H-imidazol-5-yl}-N-methylpyrimidin-2-amine (5) in Example 5. 4-{1-[1-(Isoxazol-3-ylmethyl)piperidin-4-yl]-4-phenyl-1H-imidazol-5-yl}pyrimidin-2-amine (free base of 13) was obtained as a yellow solid. Yield: 101 mg, 0.252 mmol, 29%. $^1$H NMR (400 MHz, CDCl$_3$) δ 1.97-2.08 (m, 2H), 2.12-2.24 (m, 4H), 3.03 (br d, J=12 Hz, 2H), 3.69 (s, 2H), 4.59 (tt, J=11.8, 4.0 Hz, 1H), 5.07 (br s, 2H), 6.41 (d, J=1.7 Hz, 1H), 6.54 (d, J=5.2 Hz, 1H), 7.27-7.34 (m, 3H), 7.46-7.50 (m, 2H), 7.78 (s, 1H), 8.17 (d, J=5.2 Hz, 1H), 8.40 (br d, J=1.5 Hz, 1H). This solid was dissolved in ethyl acetate, treated with a solution of hydrogen chloride in diethyl ether (2 N, 1 equivalent) and allowed to stir for 18 hours. The resulting solid was collected by filtration to provide the title product as a light yellow solid. Yield: 70 mg, 0.16 mmol, 19%.

Example 14

4-{4-(4-Fluorophenyl)-1-[1-(isoxazol-3-ylmethyl)piperidin-4-yl]-2-methyl-1H-imidazol-5-yl}pyrimidine (14)

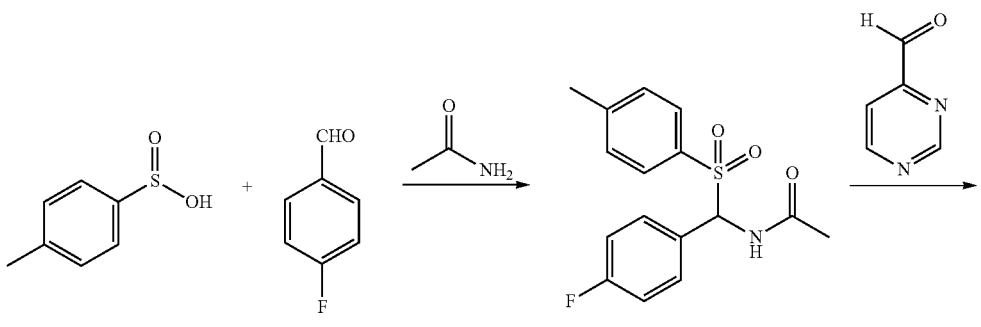

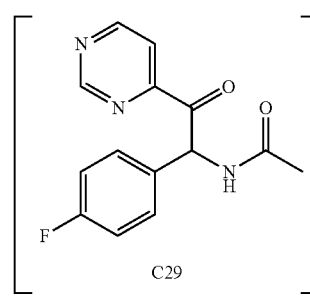

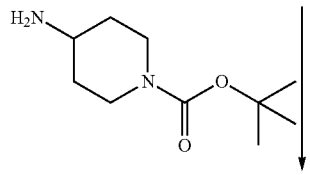

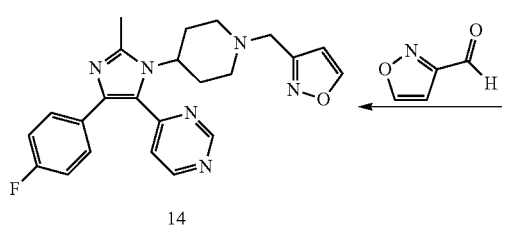
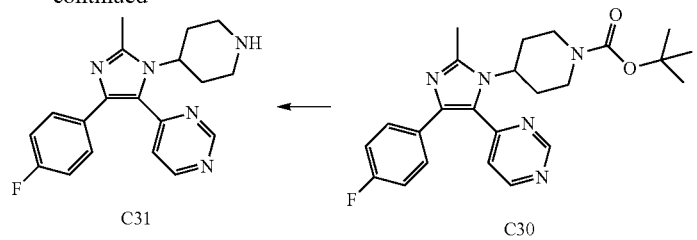

N-{(4-Fluorophenyl)[(4-methylphenyl)sulfonyl]methyl}acetamide (C28)

A mixture of 4-fluorobenzaldehyde (3.18 g, 25.6 mmol), acetamide (3.78 g, 64.0 mmol) and trimethylsilyl chloride (3.58 mL, 28.2 mmol) in acetonitrile (12 mL) and toluene (12 mL) was heated at 50° C. for 1 hour. Additional acetamide (1.28 g, 21.7 mmol) and trimethylsilyl chloride (1.2 mL, 9.5 mmol) were added, and heating was continued for 90 minutes, at which point 4-methylbenzenesulfinic acid (6.00 g, 38.4 mmol) was added. The reaction was allowed to proceed at 50° C. for 18 hours, then was cooled to room temperature and diluted with tert-butyl methyl ether (20 mL). After 5 minutes of stirring, the mixture was further diluted with water (100 mL), cooled to 0° C. for 1 hour and filtered; the collected solid was rinsed with tert-butyl methyl ether. The product was obtained as a white solid. Yield: 4.276 g, 13.3 mmol, 52%. $^1$H NMR (400 MHz, DMSO-$d_6$) δ 1.77 (s, 3H), 2.41 (s, 3H), 6.34 (d, J=10.5 Hz, 1H), 7.27 (dd, J=8.9, 8.9 Hz, 2H), 7.43 (d, J=8.0 Hz, 2H), 7.65 (dd, J=8.8, 5.5 Hz, 2H), 7.70 (d, J=8.3 Hz, 2H), 9.39 (d, J=10.5 Hz, 1H).

tert-Butyl 4-[4-(4-fluorophenyl)-2-methyl-5-pyrimidin-4-yl-1H-imidazol-1-yl]piperidine-1-carboxylate (C30)

According to the method of J. A. Murry et al., *J. Am. Chem. Soc.* 2001, 123, 9696-9697, N-{(4-fluorophenyl)[(4-methylphenyl)sulfonyl]methyl}acetamide (C28) (250 mg, 0.778 mmol) and 5-(2-hydroxyethyl)-3,4-dimethyl-1,3-thiazol-3-ium iodide (44.5 mg, 0.156 mmol) were combined, and the reaction flask was evacuated and refilled with nitrogen gas twice. Dichloromethane (4 mL) was added, followed by pyrimidine-4-carbaldehyde (92.5 mg, 0.856 mmol), and the reaction mixture was heated to 35-40° C., then treated with triethylamine (1.63 mL, 11.7 mmol); the reaction was stirred at 35° C. for 1 hour, then cooled to room temperature. Aliquot: LCMS m/z 274.5 [(M+1) for N-[1-(4-fluorophenyl)-2-oxo-2-pyrimidin-4-ylethyl]acetamide (C29)]. After 2 hours at room temperature, the mixture was concentrated in vacuo, dissolved in ethanol (4 mL) and treated with acetic acid (0.22 mL, 3.8 mmol) and tert-butyl 4-aminopiperidine-1-carboxylate (358 mg, 1.79 mmol). The reaction was heated to reflux for 3 hours, then concentrated under reduced pressure and diluted with ethyl acetate and aqueous sodium bicarbonate solution until the mixture was basic. The mixture was extracted with ethyl acetate, and the combined organic layers were dried over sodium sulfate, filtered and concentrated in vacuo. Purification of the residue by silica gel chromatography (Eluant: 5% methanol in ethyl acetate) provided the product. Yield: 60 mg, 0.14 mmol, 18%. LCMS m/z 438.6 (M+1). $^1$H NMR (400 MHz, CDCl$_3$) δ 1.48 (s, 9H), 1.95-2.00 (m, 2H), 2.12-2.23 (m, 2H), 2.61 (s, 3H), 2.68-2.77 (m, 2H), 4.21-4.33 (m, 2H), 4.65 (tt, J=12.4, 3.9 Hz, 1H), 6.97 (dd, J=8.7, 8.7 Hz, 2H), 7.12 (dd, J=5.2, 1.4 Hz, 1H), 7.29 (dd, J=8.8, 5.5 Hz, 2H), 8.54 (d, J=5.3 Hz, 1H), 9.27 (d, J=1.3 Hz, 1H).

4-[4-(4-Fluorophenyl)-2-methyl-1-piperidin-4-yl-1H-imidazol-5-yl]pyrimidine (C31)

The title compound was prepared from tert-butyl 4-[4-(4-fluorophenyl)-2-methyl-5-pyrimidin-4-yl-1H-imidazol-1-yl]piperidine-1-carboxylate (C30) according to the general procedure for the synthesis of N-methyl-4-(4-phenyl-1-piperidin-4-yl-1H-imidazol-5-yl)pyrimidin-2-amine (C26) in Example 12, except in this case the extraction was carried out with dichloromethane. Yield: 35.7 mg, 0.106 mmol, 50%. LCMS m/z 338.5 (M+1). $^1$H NMR (400 MHz, CDCl$_3$) δ 1.96-2.01 (m, 2H), 2.14-2.24 (m, 3H), 2.61-2.68 (m, 2H), 2.65 (s, 3H), 3.19-3.24 (m, 2H), 4.57 (tt, J=12.3, 3.9 Hz, 1H), 6.96 (dd, J=8.8, 8.8 Hz, 2H), 7.12 (dd, J=5.3, 1.4 Hz, 1H), 7.29 (dd, J=8.9, 5.5 Hz, 2H), 8.55 (d, J=5.3 Hz, 1H), 9.30 (d, J=1.3 Hz, 1H).

4-{4-(4-Fluorophenyl)-1-[1-(isoxazol-3-ylmethyl)piperidin-4-yl]-2-methyl-1H-imidazol-5-yl}pyrimidine (14)

Compound 14 was prepared from 4-[4-(4-fluorophenyl)-2-methyl-1-piperidin-4-yl-1H-imidazol-5-yl]pyrimidine (C31) according to the general procedure for the synthesis of 4-{4-(4-fluorophenyl)-1-[1-(isoxazol-3-ylmethyl)piperidin-4-yl]-1H-imidazol-5-yl}-N-methylpyrimidin-2-amine (5) in Example 5, except that extractions were carried out with dichloromethane, and the eluant employed for chromatography was 5% methanol in dichloromethane. The product was obtained as a solid. Yield: 10 mg, 0.024 mmol, 23%. LCMS m/z 419.6 (M+1). $^1$H NMR (400 MHz, CDCl$_3$) δ 1.95-2.00 (m, 2H), 2.15 (ddd, J=11.8, 11.8, 2.0 Hz, 2H), 2.27-2.37 (m, 2H), 2.65 (s, 3H), 3.01 (br d, J=11.6 Hz, 2H), 3.67 (s, 2H), 4.48 (tt, J=12.4, 4.0 Hz, 1H), 6.39 (d, J=1.7 Hz, 1H), 6.96 (dd, J=8.8, 8.8 Hz, 2H), 7.12 (dd, J=5.3, 1.5 Hz, 1H), 7.29 (dd, J=8.8, 5.4 Hz, 2H), 8.38 (d, J=1.7 Hz, 1H), 8.55 (d, J=5.3 Hz, 1H), 9.30 (d, J=1.4 Hz, 1H).

The structures of additional Examples are shown in Tables 1 and 2. Tables 1 and 2 give physical data and preparative information for these additional Examples, and Table 3 contains relevant biological data for all Examples.

Methods

Method A

Reductive amination, exemplified by synthesis of 4-{4-(4-fluorophenyl)-1-[(1-substituted)piperidin-4-yl]-1H-imidazol-5-yl}pyrimidines (Example 29)

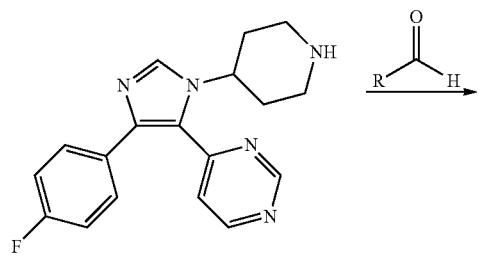

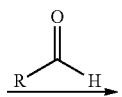

C15

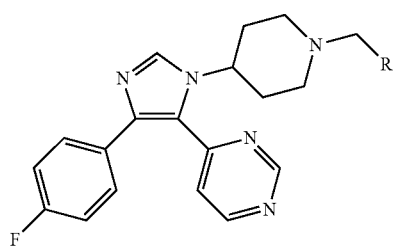

A solution of 4-[4-(4-fluorophenyl)-1-piperidin-4-yl-1H-imidazol-5-yl]pyrimidine (C15) (0.068 mmol) in dichloroethane (1 mL) was added to a vial containing the appropriate aldehyde (0.075 mmol), and the mixture was treated with triethylamine (0.15 mmol) and acetic acid (0.38 mmol). The vial was shaken for 30 minutes, at which time sodium triacetoxyborohydride (0.22 mmol) was added and shaking was continued for an additional 66 hours. The reaction was quenched with aqueous sodium hydroxide solution (1 N, 2 mL), added to dichloroethane (2 mL) and shaken. The organic layer was separated and filtered through an empty solid-phase extraction cartridge, and the filtrate was concentrated in vacuo. The residue was dissolved in dimethyl sulfoxide (1 mL) and purified by reversed-phase HPLC (Column: Waters XBridge $C_{18}$, 5 μm; Mobile phase A: 0.03% $NH_4OH$ in water (v/v); Mobile phase B: 0.03% $NH_4OH$ in acetonitrile (v/v); Gradient: 15% to 95% B). See Table 2 for characterization data; biological activity is provided in Table 3.

Method B

Reductive amination, exemplified by synthesis of 4-[4-(4-fluorophenyl)-1-[(1-substituted)piperidin-4-yl]-1H-imidazol-5-yl]pyrimidin-2-amines, trifluoroacetate salts (Examples 17-28)

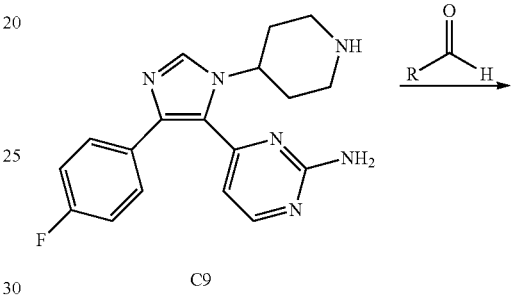

C9

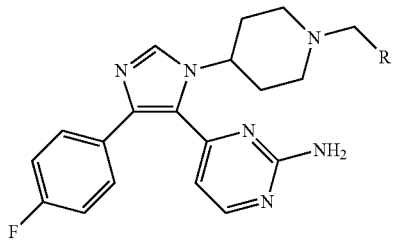

A slurry of 4-[4-(4-fluorophenyl)-1-piperidin-4-yl-1H-imidazol-5-yl]pyrimidin-2-amine, hydrochloride salt (C9) (0.075 mmol) in a 1:1 mixture of DMF and dichloromethane (0.50 mL) was added to a vial containing the appropriate aldehyde (0.075 mmol). Sodium triacetoxyborohydride (approximately 50 mg, 0.24 mmol) was added and the mixture was shaken for 18 hours. Aqueous sodium hydroxide solution (1 N, 1.5 mL) was added, followed by dichloromethane (2.0 mL), and the vial was vortexed for 15 minutes. The aqueous layer was extracted with dichloromethane (2×1.0 mL), and the combined organic layers were concentrated in vacuo. Dimethyl sulfoxide (0.5 mL) was added, the sample was filtered, diluted with additional dimethyl sulfoxide (0.5 mL) and purified by reversed-phase HPLC (Column: Waters Sunfire $C_{18}$, 5 μm; Mobile phase A: 0.05% TFA in water (v/v); Mobile phase B: 0.05% TFA in acetonitrile (v/v); Gradient: 5% to 95% B). See Table 2 for characterization data; biological activity is provided in Table 3.

Kinase Assay.

The CK1δ kinase assay was performed in a standard buffer containing ATP at 10 μM, CK1δ enzyme at 2 nM, and the peptide substrate PLSRTLpSVASLPGL at 42 μM. The reaction was incubated at 25° C. for 85 minutes. Enzyme inhibition was performed in the presence of either 1 μL of CK1δ inhibitor, or 4% DMSO. Detection of luminescent output on a PerkinElmer EnVision plate reader (PerkinElmer, Waltham, Mass.) was performed as described for the Kinase-Glo Assay (Promega).

The CK1ε kinase assay was performed in a standard buffer containing ATP at 10 μM, CK1ε wild type enzyme at 2.5 nM, and 42 μM concentration of the peptide substrate PLSRTLpS-VASLPGL (Flotow et al., 1990). The reaction was incubated at 25° C. for 70 minutes. Enzyme inhibition was measured in the presence of 1 μL of the CK1ε inhibitor, or 4% DMSO. Detection was carried out as described for the Kinase-Glo Assay (Promega). Luminescent output was measured on the PerkinElmer EnVision plate reader (PerkinElmer, Waltham, Mass.).

TABLE 1

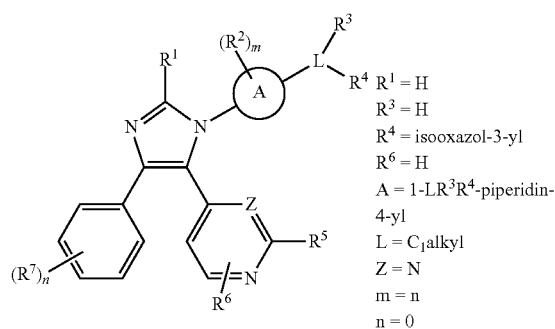

$R^1$ = H
$R^3$ = H
$R^4$ = isooxazol-3-yl
$R^6$ = H
A = 1-L$R^3R^4$-piperidin-4-yl
L = $C_1$alkyl
Z = N
m = n
n = 0

| Ex# | $R_5$ | Method; starting material | IUPAC Name | $^1$H NMR (400 MHz, CDCl$_3$), δ (ppm); Mass spectrum: APCI, observed ion m/z |
|---|---|---|---|---|
| 15 | NHMe | Ex. 5: C26 | 4-{1-[1-(isoxazol-3-ylmethyl)piperidin-4-yl]-4-phenyl-1H-imidazol-5-yl}-N-methylpyrimidin-2-amine, hydrochloride salt | 1.99-2.10 (m, 2H), 2.15-2.22 (m, 4H), 3.01-3.06 (m, 2H), 3.05 (d, J = 5.1 Hz, 3H), 3.69 (s, 2H), 4.69 (br s, 1H), 5.18-5.21 (m, 1H), 6.41 (d, J = 1.6 Hz, 1H), 6.44 (d, J = 5.1 Hz, 1H), 7.26-7.33 (m, 3H), 7.48-7.51 (m, 2H), 7.79 (s, 1H), 8.14 (br d, J = 4.9 Hz, 1H), 8.39 (d, J = 1.6 Hz, 1H); 416.3 (M + 1)$^1$ |
| 16 | H | Ex. 5; C23 | 4-{1-[1-(isoxazol-3-ylmethyl)piperidin-4-yl]-4-phenyl-1H-imidazol-5-yl}pyrimidine | 1.99-2.09 (m, 2H), 2.13-2.18 (m, 2H), 2.23 (ddd, J = 11.9, 11.9, 2.1 Hz, 2H), 3.03 (br d, J = 11.9, 2H), 3.70 (s, 2H), 4,75 (tt, J = 11.9, 4.1 Hz, 1H), 6.40 (d, J = 1.7 Hz, 1H), 7.18 (dd, J = 5.3, 1.4 Hz, 1H), 7.30-7.35 (m, 3H), 7.41-7.44 (m, 2H), 7.84 (s, 1H), 8.39 (br d, J = 1.6 Hz, 1H), 8.53 (d, J = 5.4 Hz, 1H), 9.28 (d, J = 1.4 Hz, 1H); 387.1 (M + 1) |

$^1$NMR and MS data obtained on free base, prior to formation of hydrochloride salt.

TABLE 2

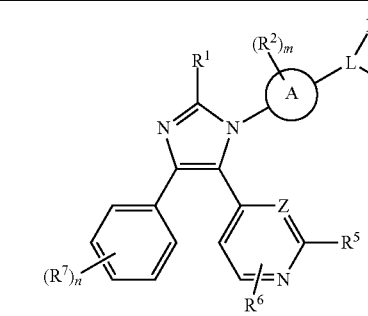

R¹ = H
R⁶ = H
R⁷ = F
n = 1 (para)
Z = N

| Ex# | Method; starting material | 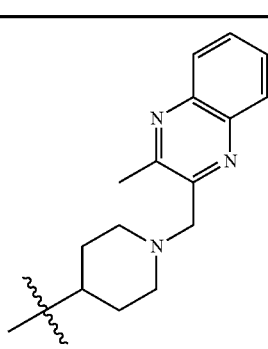 | R₅ | IUPAC Name | Retention Time (min) [HPLC method in footnotes] | Mass spectrum: Observed ion m/z (M + 1) or (M + 2)/2 |
|---|---|---|---|---|---|---|
| 17 | B; C9 | 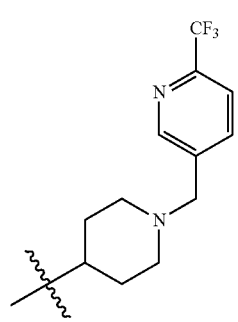 [SMILES: *C1CCN(Cc2ccc(C(F)(F)F)nc2)CC1] | NH₂ | 4-[4-(4-fluorophenyl)-1-{1-[(3-methylquinoxalin-2-yl)methyl]piperidin-4-yl}-1H-imidazol-5-yl]pyrimidin-2-amine, trifluoroacetate salt | 1.05² | 495.16 |
| 18 | B; C9 | 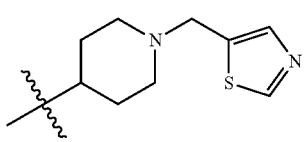 [SMILES: *C1CCN(Cc2cncs2)CC1] | NH₂ | 4-[4-(4-fluorophenyl)-1-(1-{[6-(trifluoromethyl)pyridin-3-yl]methyl}piperidin-4-yl)-1H-imidazol-5-yl]pyrimidin-2-amine, trifluoroacetate salt | 1.05² | 498.10 |
| 19 | B; C9 | 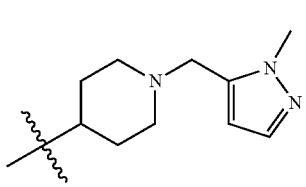 [SMILES: *C1CCN(Cc2ccnn2C)CC1] | NH₂ | 4-{4-(4-fluorophenyl)-1-[1-(1,3-thiazol-5-ylmethyl)piperidin-4-yl]-1H-imidazol-5-yl}pyrimidin-2-amine, trifluoroacetate salt | 0.88² | 436.11 |
| 20 | B; C9 | 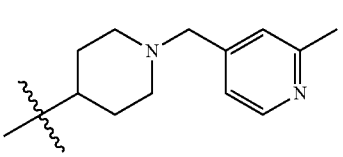 [SMILES: *C1CCN(Cc2ccnc(C)c2)CC1] | NH₂ | 4-[4-(4-fluorophenyl)-1-{1-[(1-methyl-1H-pyrazol-5-yl)methyl]piperidin-4-yl}-1H-imidazol-5-yl]pyrimidin-2-amine, trifluoroacetate salt | 0.90² | 433.17 |
| 21 | B; C9 | | NH₂ | 4-[4-(4-fluorophenyl)-1-{1-[(2-methylpyridin-4-yl)methyl]piperidin-4-yl}-1H-imidazol-5-yl]pyrimidin-2-amine, trifluoroacetate salt | 0.85² | 444.18 |

TABLE 2-continued

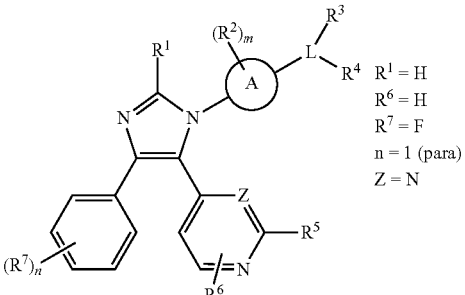

R¹ = H
R⁶ = H
R⁷ = F
n = 1 (para)
Z = N

| Ex# | Method; starting material | 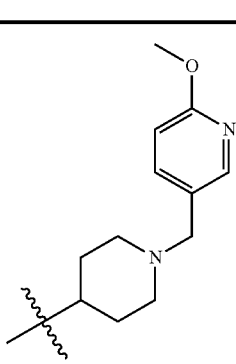 | R₅ | IUPAC Name | Retention Time (min) [HPLC method in footnotes] | Mass spectrum: Observed ion m/z (M + 1) or (M + 2)/2 |
|---|---|---|---|---|---|---|
| 22 | B; C9 | 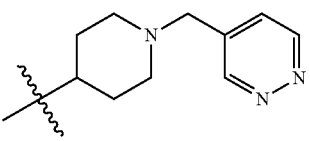 [SMILES: *C1CCN(Cc2ccnnc2)CC1] | NH₂ | 4-[4-(4-fluorophenyl)-1-{1-[(6-methoxypyridin-3-yl)methyl]piperidin-4-yl}-1H-imidazol-5-yl]pyrimidin-2-amine, trifluoroacetate salt | 0.97² | 460.16 |
| 23 | B; C9 | 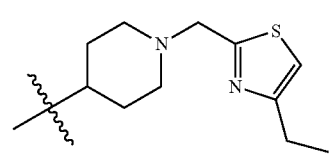 [SMILES: *C1CCN(Cc2nc(CC)cs2)CC1] | NH₂ | 4-{4-(4-fluorophenyl)-1-[1-(pyridazin-4-ylmethyl)piperidin-4-yl]-1H-imidazol-5-yl}pyrimidin-2-amine, trifluoroacetate salt | 0.88² | 431.15 |
| 24 | B; C9 | 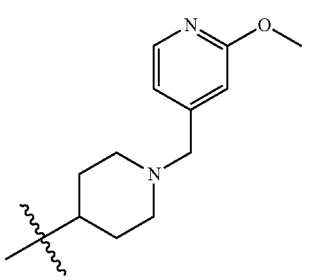 [SMILES: *C1CCN(Cc2ccnc(OC)c2)CC1] | NH₂ | 4-[1-{1-[(4-ethyl-1,3-thiazol-2-yl)methyl]piperidin-4-yl}-4-(4-fluorophenyl)-1H-imidazol-5-yl]pyrimidin-2-amine, trifluoroacetate salt | 1.02² | 464.13 |
| 25 | B; C9 |  | NH₂ | 4-[4-(4-fluorophenyl)-1-{1-[(2-methoxypyridin-4-yl)methyl]piperidin-4-yl}-1H-imidazol-5-yl]pyrimidin-2-amine, trifluoroacetate salt | 0.97² | 460.16 |

TABLE 2-continued

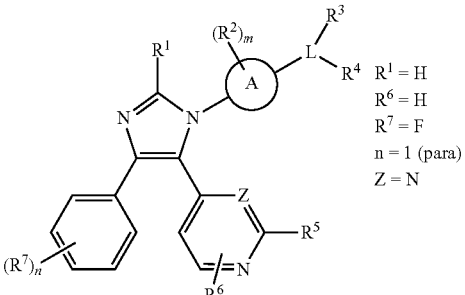

| Ex# | Method; starting material | (R²)ₘ—A—L(R³)(R⁴) | R₅ | IUPAC Name | Retention Time (min) [HPLC method in footnotes] | Mass spectrum: Observed ion m/z (M + 1) or (M + 2)/2 |
|---|---|---|---|---|---|---|
| 26 | B; C9 | 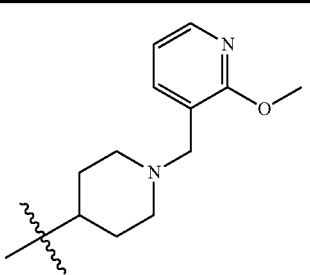 | NH₂ | 4-[4-(4-fluorophenyl)-1-{1-[(2-methoxypyridin-3-yl)methyl]piperidin-4-yl}-1H-imidazol-5-yl]pyrimidin-2-amine, trifluoroacetate salt | 0.96² | 460.16 |
| 27 | B; C9 | 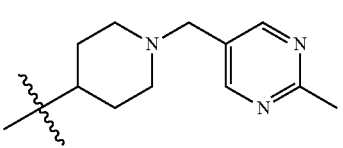 [SMILES: *C1CCN(Cc2cnc(C)nc2)CC1] | NH₂ | 4-[4-(4-fluorophenyl)-1-{1-[(2-methylpyrimidin-5-yl)methyl]piperidin-4-yl}-1H-imidazol-5-yl]pyrimidin-2-amine, trifluoroacetate salt | 0.89² | 445.17 |
| 28 | B; C9 | 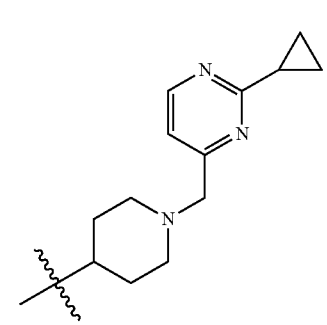 [SMILES: *C1CCN(Cc2ccnc(C3CC3)n2)CC1] | NH₂ | 4-[1-{1-[(2-cyclopropylpyrimidin-4-yl)methyl]piperidin-4-yl}-4-(4-fluorophenyl)-1H-imidazol-5-yl]pyrimidin-2-amine, trifluoroacetate salt | 0.99² | 471.18 |
| 29 | A; C15 | 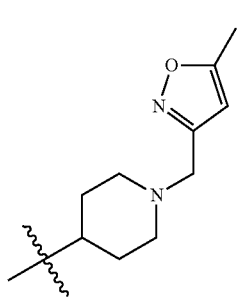 [SMILES: *C1CCN(Cc2cc(C)on2)CC1] | H | 4-[4-(4-fluorophenyl)-1-{1-[(5-methylisoxazol-3-yl)methyl]piperidin-4-yl}-1H-imidazol-5-yl]pyrimidine | 2.14³ | 419.22 |

TABLE 2-continued

Structure with R¹ = H, R⁶ = H, R⁷ = F, n = 1 (para), Z = N

| Ex# | Method; starting material | [A/L/R³/R⁴ group] | R₅ | IUPAC Name | Retention Time (min) [HPLC method in footnotes] | Mass spectrum: Observed ion m/z (M + 1) or (M + 2)/2 |
|---|---|---|---|---|---|---|
| 30 | B⁴; C18 | pyrrolidin-3-yl-CH₂-(6-methylpyridin-2-yl) | NH₂ | 4-[4-(4-fluorophenyl)-1-{1-[(6-methylpyridin-2-yl)methyl]pyrrolidin-3-yl}-1H-imidazol-5-yl]pyrimidin-2-amine | 2.22[1] | 430.24 |
| 31 | B⁴; C18 | pyrrolidin-3-yl-CH₂-(3-fluoro-5-methylpyridin-2-yl) | NH₂ | 4-[1-{1-[(3-fluoro-5-methylpyridin-2-yl)methyl]pyrrolidin-3-yl}-4-(4-fluorophenyl)-1H-imidazol-5-yl]pyrimidin-2-amine | 2.32[1] | 448.23 |
| 32 | B⁴; C18 | pyrrolidin-3-yl-CH₂-(2-methylpyridin-3-yl) | NH₂ | 4-[4-(4-fluorophenyl)-1-{1-[(2-methylpyridin-3-yl)methyl]pyrrolidin-3-yl}-1H-imidazol-5-yl]pyrimidin-2-amine | 2.18[1] | 430.24 |
| 33 | B⁴; C18 | pyrrolidin-3-yl-CH₂-(5-methylisoxazol-3-yl) | NH₂ | 4-[4-(4-fluorophenyl)-1-{1-[(5-methylisoxazol-3-yl)methyl]pyrrolidin-3-yl}-1H-imidazol-5-yl]pyrimidin-2-amine | 2.21[1] | 420.23 |
| 34 | B⁴; C18 | pyrrolidin-3-yl-CH₂-(pyridin-4-yl) | NH₂ | 4-{4-(4-fluorophenyl)-1-[1-(pyridin-4-ylmethyl)pyrrolidin-3-yl]-1H-imidazol-5-yl}pyrimidin-2-amine | 2.05[1] | 416.23 |

… TABLE 2-continued

| Ex# | Method; starting material | A (R₅ substituent structure) | R₅ | IUPAC Name | Retention Time (min) [HPLC method in footnotes] | Mass spectrum: Observed ion m/z (M + 1) or (M + 2)/2 |
|---|---|---|---|---|---|---|
| 35 | B⁴; C18 | quinoxalin-6-ylmethyl-pyrrolidin-3-yl | NH₂ | 4-{4-(4-fluorophenyl)-1-[1-(quinoxalin-6-ylmethyl)pyrrolidin-3-yl]-1H-imidazol-5-yl}pyrimidin-2-amine | 2.21[1] | 467.22 |
| 36 | B⁴; C18 | isoquinolin-4-ylmethyl-pyrrolidin-3-yl | NH₂ | 4-{4-(4-fluorophenyl)-1-[1-(isoquinolin-4-ylmethyl)pyrrolidin-3-yl]-1H-imidazol-5-yl}pyrimidin-2-amine | 2.45[1] | 466.25 |
| 37 | B⁴; C18 | (4,6-dimethylpyridin-3-yl)methyl-pyrrolidin-3-yl | NH₂ | 4-[1-{1-[(4,6-dimethylpyridin-3-yl)methyl]pyrrolidin-3-yl}-4-(4-fluorophenyl)-1H-imidazol-5-yl]pyrimidin-2-amine | 2.35[1] | 444.24 |
| 38 | B⁴; C18 | 1,5-naphthyridin-4-ylmethyl-pyrrolidin-3-yl | NH₂ | 4-{4-(4-fluorophenyl)-1-[1-(1,5-naphthyridin-4-ylmethyl)pyrrolidin-3-yl]-1H-imidazol-5-yl}pyrimidin-2-amine | 2.12[1] | 467.22 |

TABLE 2-continued

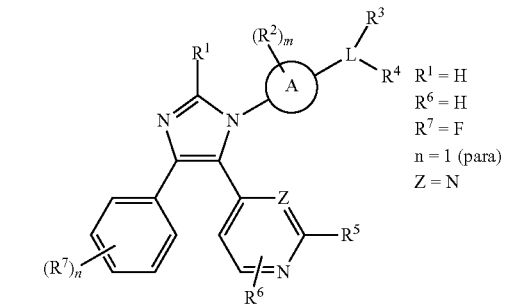

R¹ = H
R⁶ = H
R⁷ = F
n = 1 (para)
Z = N

| Ex# | Method; starting material | (R²)ₘ–A–L(R³)(R⁴) group | R₅ | IUPAC Name | Retention Time (min) [HPLC method in footnotes] | Mass spectrum: Observed ion m/z (M + 1) or (M + 2)/2 |
|---|---|---|---|---|---|---|
| 39 | A; C20 | 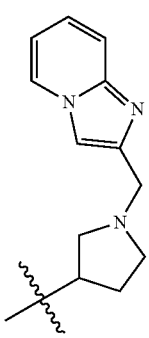 [SMILES: *C1CCN(Cc2cn3ccccc3n2)C1] | H | 2-({3-[4-(4-fluorophenyl)-5-pyrimidin-4-yl-1H-imidazol-1-yl]pyrrolidin-1-yl}methyl)imidazo[1,2-a]pyridine, trifluoroacetate salt | 1.68[5] | 220.84 |
| 40 | A; C20 | 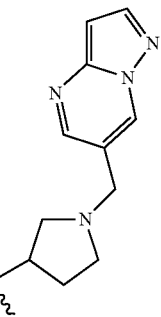 | H | 6-({3-[4-(4-fluorophenyl)-5-pyrimidin-4-yl-1H-imidazol-1-yl]pyrrolidin-1-yl}methyl)pyrazolo[1,5-a]pyrimidine, trifluoroacetate salt | 1.76[5] | 441.19 |
| 41 | A; C20 | 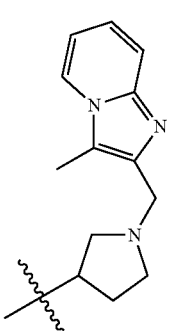 [SMILES: *C1CCN(Cc2nc3ccccn3c2C)C1] | H | 2-({3-[4-(4-fluorophenyl)-5-pyrimidin-4-yl-1H-imidazol-1-yl]pyrrolidin-1-yl}methyl)-3-methylimidazo[1,2-a]pyridine, trifluoroacetate salt | 1.69[5] | 454.18 |

TABLE 2-continued

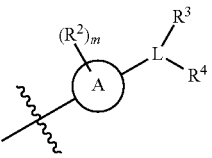

| Ex# | Method; starting material | R₅ structure | $R_5$ | IUPAC Name | Retention Time (min) [HPLC method in footnotes] | Mass spectrum: Observed ion m/z (M + 1) or (M + 2)/2 |
|---|---|---|---|---|---|---|
| 42 | A; C20 | (shown) | H | 5-({3-[4-(4-fluorophenyl)-5-pyrimidin-4-yl-1H-imidazol-1-yl]pyrrolidin-1-yl}methyl)-2-(2-methoxyethyl)pyrimidine, trifluoroacetate salt | 1.72[5] | 460.18 |

[1] Analytical HPLC Method-Colomn: Water XBridge $C_{18}$, 4.6 × 50 mm, 3.5 μm; Mobile phase A: 0.1% NH₄OH in water (v/v); Mobile phase B: 0.1% NH₄OH in acetonitrile (v/v); Flow rate 2 mL/min.
Gradient:
0 minutes 5% B
4 minutes 95% B
5 minutes 95% B

[2] Analytical HPLC Method-Column: Advanced Materials Technology Halo $C_{18}$, 3.0 × 30 mm, 2.7 μm; Mobile phase A: 0.01% TFA in water (v/v); Mobile phase B: 0.01% TFA in acetonitrile (v/v); Flow rate 1.5 mL/min.
Gradient:
0 minutes 5% B
2.3 minutes 95% B
2.5 minutes 95% B

[3] Analytical HPLC Method-Colomn: Water XBridge $C_{18}$, 4.6 × 50 mm, 3.5 μm; Mobile phase A: 0.1% NH₄OH in water (v/v); Mobile phase B: 0.1% NH₄OH in acetonitrile (v/v); Flow rate 2 mL/min.
Gradient:
0 minutes 10% B
4 minutes 95% B
5 minutes 95% B

[4] Preparative HPLC purification in this case was carried out as described in Method A.

[5] Analytical HPLC Method-Colomn: Water Atlantis $dC_{18}$, 4.6 × 50 mm, 5 μm; Mobile phase A: 0.1% TFA in water (v/v); Mobile phase B: 0.1% TFA in acetonitrile (v/v); Flow rate 2 mL/min.
Gradient:
0 minutes 5% B
4 minutes 95% B
5 minutes 95% B

TABLE 3

Biological Data for Examples 1-42

| Ex # | CKIδ IC₅₀ (nM), geometric mean of 2-4 determinations | CKIε IC₅₀ (nM), geometric mean of 2-4 determinations |
|---|---|---|
| 1 | 163 | 536 |
| 2 | 16.7 | 67.4 |
| 3 | 27.8 | 116 |
| 4 | <4.17* | 18.9* |

TABLE 3-continued

Biological Data for Examples 1-42

| Ex # | CKIδ IC$_{50}$ (nM), geometric mean of 2-4 determinations | CKIε IC$_{50}$ (nM), geometric mean of 2-4 determinations |
|---|---|---|
| 5 | 6.86* | 32.3* |
| 6 | 24.0* | 126* |
| 7 | 67.8 | 193 |
| 8 | 211* | 617* |
| 9 | 281 | 1360 |
| 10 | 64.6 | 277 |
| 11 | 790 | >3660 |
| 12 | 191 | 660 |
| 13 | 8.22 | 40.9 |
| 14 | 140 | 829 |
| 15 | 18.6 | 76.1 |
| 16 | 42.8 | 327 |
| 17 | 32.1 | 144 |
| 18 | 80.7 | 394 |
| 19 | 26.8 | 99.9 |
| 20 | 42.8 | 244 |
| 21 | 13.0 | 59.8 |
| 22 | 83.6 | 482 |
| 23 | 8.51 | 34.8 |
| 24 | 83.7 | 382 |
| 25 | 84.3 | 393 |
| 26 | 51.9 | 238 |
| 27 | 17.6 | 83.2 |
| 28 | 54.9 | 351 |
| 29 | 38.8 | 268 |
| 30 | 91.6 | 266 |
| 31 | 47.6 | 165 |
| 32 | 61.1 | 150 |
| 33 | 55.1 | 140 |
| 34 | 76.6 | 211 |
| 35 | 67.8 | 170 |
| 36 | 56.3 | 140 |
| 37 | 46.6 | 124 |
| 38 | 55.8 | 158 |
| 39 | 211 | 644 |
| 40 | 178 | 798 |
| 41 | 595 | 1990 |
| 42 | 679 | 1530 |

*Geometric mean of 5-16 determinations

We claim:

1. A compound of formula I:

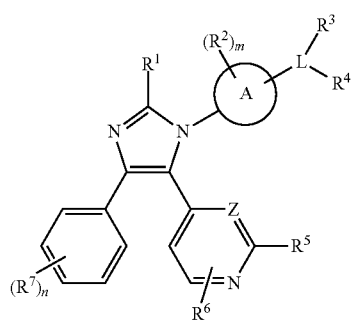

or a pharmaceutically acceptable salt thereof wherein:
A is a nitrogen-containing 4- to 7-membered heterocycloalkyl;
L is $C_{1-3}$alkyl;
$R^1$ is hydrogen, $C_{1-3}$alkyl, or $C_{3-4}$cycloalkyl;
each $R^2$ is independently $C_{1-3}$alkyl, fluorine, hydroxyl, $C_{1-3}$alkoxy, or cyano;
$R^3$ is hydrogen, $C_{1-3}$alkyl, or $C_{3-4}$cycloalkyl;
$R^4$ is a 5- to 10-membered heteroaryl with 1 to 3 heteroatoms, optionally substituted with 1 to 3 $R^7$ substituents;
$R^5$ is hydrogen or $-N(R^8)_2$;
$R^6$ is hydrogen, halogen or $C_{1-3}$alkyl;
each $R^7$ is independently halogen, $-(CH_2)_t-F$, $C_{1-3}$alkyl, $-CF_3$, $-(CH_2)_t-C_{3-4}$cycloalkyl, $-(CH_2)_t-O-C_{1-3}$alkyl, $-(CH_2)_t$-cyano or $-(CH_2)_t$-hydroxy;
Z is N or $-CR^9$;
each $R^8$ is independently hydrogen or $C_{1-3}$alkyl;
$R^9$ is hydrogen, $C_{1-3}$alkyl, or halogen;
m is 0, 1 or 2;
n is 0, 1, or 2; and
t is 0, 1 or 2.

2. A compound of claim 1 wherein

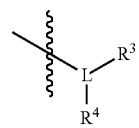

is attached to a ring N of ring A;
L is $C_1$alkyl;
each $R^2$ is independently $C_{1-3}$alkyl, or fluorine; and
each $R^7$ is independently halogen, $-(CH_2)_t-F$, $C_{1-3}$alkyl, $-CF_3$, $-(CH_2)_t-C_{3-4}$cycloalkyl, or $-(CH_2)_t-O-C_{1-3}$alkyl.

3. A compound of claim 2 wherein A is a nitrogen-containing 5-membered heterocycloalkyl wherein said heterocycloalkyl is pyrrolidine and

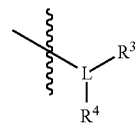

is attached to the ring N of the pyrrolidine, and m is zero.

4. A compound of claim 2 wherein A is a nitrogen-containing 6-membered heterocycloalkyl wherein said heterocycloalkyl is piperidine and

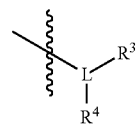

is attached to the ring N of the piperidine, and m is zero.

5. A compound of claim 2 wherein n is 1, and $R^7$ is fluorine.

6. A compound of claim 1 wherein Z is N and $R^5$ is $-N(R^8)_2$, wherein each $R^8$ is hydrogen.

7. A compound of claim 1 wherein $R^1$ is hydrogen or $C_{1-3}$alkyl.

8. A compound of claim 1 wherein $R^4$ is a 5-membered heteroaryl wherein said heteroaryl is an isoxazole optionally substituted with 1 or 2 $R^7$ substituents, and t is zero.

9. A compound of claim 1 wherein $R^3$ is hydrogen or $C_{1-3}$alkyl.

10. A method for treating a disorder that is selected from the group consisting of a mood disorder and a sleep disorder in a mammal, which method comprises administering to the mammal a therapeutically effective amount of a compound of claim 1 or a pharmaceutically acceptable salt thereof.

11. The method according to claim 10 wherein the disorder to be treated is a mood disorder that is selected from the group consisting of a depressive disorder and a bipolar disorder.

12. A pharmaceutical composition comprising a compound of claim 1 or a pharmaceutically acceptable salt thereof, and a pharmaceutically acceptable carrier.

13. A compound selected from the group consisting of:
- 4-{4-(4-Fluorophenyl)-1-[1-(pyrimidin-2-ylmethyl)piperidin-4-yl]-1H-imidazol-5-yl}pyrimidin-2-amine;
- 4-{4-(4-Fluorophenyl)-1-[1-(isoxazol-3-ylmethyl)piperidin-4-yl]-1H-imidazol-5-yl}pyrimidin-2-amine;
- 4-{4-(4-Fluorophenyl)-1-[1-(isoxazol-3-ylmethyl)piperidin-4-yl]-1H-imidazol-5-yl}-N-methylpyrimidin-2-amine;
- 4-{4-(4-Fluorophenyl)-1-[1-(isoxazol-3-ylmethyl)piperidin-4-yl]-1H-imidazol-5-yl}pyrimidine;
- 4-{4-(4-Fluorophenyl)-1-[1-(isoxazol-3-ylmethyl)pyrrolidin-3-yl]-1H-imidazol-5-yl}pyrimidin-2-amine;
- 2-{([4-(4-Phenyl-5-pyrimidin-4-yl-1H-imidazol-1-yl)piperidin-1-yl]methyl}pyrimidine;
- N-Methyl-4-{4-phenyl-1-[1-(pyrimidin-2-ylmethyl)piperidin-4-yl]-1H-imidazol-5-yl}pyrimidin-2-amine;
- 4-{1-[1-(Isoxazol-3-ylmethyl)piperidin-4-yl]-4-phenyl-1H-imidazol-5-yl}pyrimidin-2-amine;
- 4-{1-[1-(isoxazol-3-ylmethyl)piperidin-4-yl]-4-phenyl-1H-imidazol-5-yl}-N-methylpyrimidin-2-amine;
- 4-{4-(4-fluorophenyl)-1-[1-(1,3-thiazol-5-ylmethyl)piperidin-4-yl]-1H-imidazol-5-yl}pyrimidin-2-amine;
- 4-[4-(4-fluorophenyl)-1-{(1-[(2-methylpyridin-4-yl)methyl]piperidin-4-yl}-1H-imidazol-5-yl]pyrimidin-2-amine;
- 4-{4-(4-fluorophenyl)-1-[1-(pyridazin-4-ylmethyl)piperidin-4-yl]-1H-imidazol-5-yl}pyrimidin-2-amine, and
- 4-[4-(4-fluorophenyl)-1-{1-[(2-methylpyrimidin-5-yl)methyl]piperidin-4-yl}-1H-imidazol-5-yl]pyrimidin-2-amine, or a pharmaceutically acceptable salt thereof.

14. A pharmaceutical composition comprising a compound of claim 13 or a pharmaceutically acceptable salt thereof, and a pharmaceutically acceptable carrier.

15. A method for treating a disorder that is selected from the group consisting of a mood disorder and a sleep disorder in a mammal, which method comprises administering to the mammal a therapeutically effective amount of a compound of claim 13 or a pharmaceutically acceptable salt thereof.

16. The method according to claim 15 wherein the disorder to be treated is a mood disorder that is selected from the group consisting of a depressive disorder and a bipolar disorder.

17. The method according to claim 10 wherein the disorder to be treated is a mood disorder and wherein the mood disorder is a bipolar disorder.

18. The method according to claim 15 wherein the disorder to be treated is a mood disorder and wherein the mood disorder is a bipolar disorder.

* * * * *